US011345729B2

(12) United States Patent
Kim et al.

(10) Patent No.: US 11,345,729 B2
(45) Date of Patent: May 31, 2022

(54) RECOMBINANT FUSION PROTEIN OF BAF57 AND USES THEREOF

(71) Applicant: GOOD T CELLS, INC., Seoul (KR)

(72) Inventors: Jung Ho Kim, Seoul (KR); Beom Seok Kim, Seoul (KR)

(73) Assignee: GOOD T CELLS, INC., Seoul (KR)

( * ) Notice: Subject to any disclaimer, the term of this patent is extended or adjusted under 35 U.S.C. 154(b) by 0 days.

(21) Appl. No.: 16/728,216

(22) Filed: Dec. 27, 2019

(65) Prior Publication Data

US 2020/0239532 A1 Jul. 30, 2020

Related U.S. Application Data

(63) Continuation of application No. PCT/KR2018/016903, filed on Dec. 28, 2018.

(30) Foreign Application Priority Data

Dec. 28, 2017 (KR) ........................ 10-2017-0181969
Dec. 28, 2018 (KR) ........................ 10-2018-0172499

(51) Int. Cl.
*C07K 14/47* (2006.01)

(52) U.S. Cl.
CPC ...... *C07K 14/4702* (2013.01); *C07K 2319/09* (2013.01); *C07K 2319/43* (2013.01)

(58) Field of Classification Search
CPC ........................ C07K 14/4702; C07K 2319/00
See application file for complete search history.

(56) References Cited

U.S. PATENT DOCUMENTS 7,973,135 B2 * 7/2011 Liik .................. C07K 14/4705 530/387.1

FOREIGN PATENT DOCUMENTS

CN 1333288 A * 1/2002
JP 2002-356436 A 12/2002
KR 10-2012-0115913 A 10/2012

OTHER PUBLICATIONS

Moon et al. "Immuno-suppressive function of nucleus-transducible BAF57-ΔPH in T cell activation via degradation of endogenous BAF57", International Journal of Hematology, Jul. 5, 2018, pp. 375-383 (Year: 2018).*

Kabouridis "Biological applications of protein transduction technology", TRENDS in Biotechnology, 2003, pp. 498-503 (Year: 2003).*

Murriel et al. "Influence of protein transduction domains on intracellular delivery of macromolecules", Expert Opin. Drug Deliv., 2006, pp. 739-746 (Year: 2006).*

GenBank:AAC04509.1 (Year: 1998).*

GenBank: AF035262.1 (Year: 1998).*

Einhauer et al. "The FLAG peptide, a versatile fusion tag for the purification of recombinant proteins", J. Biochem. Biophys. Methods, 2001, pp. 455-465 (Year: 2001).*

International Application No. PCT/KR2018/016903, International Search Report and Written Opinion, dated Apr. 22, 2019.

NCBI GenBank Accession No. AAP36982.1, *Homo sapiens* SWI/SNF related, matrix associated, actin dependent regulator of chromatin, subfamily e, member 1, partial [synthetic construct], 1-2, (2016).

NCBI GenBank Accession No. BC007082.1, *Homo sapiens* SWI/SNF related, matrix associated, actin dependent regulator of chromatin, subfamily e, member 1, mRNA (cDNA clone MGC:14622 IMAGE:4076036), complete cds, 1-2, (2006).

Wang et al., The BRG1- and hBRM-associated factor BAF57 induces apoptosis by stimulating expression of the cylindromatosis tumor suppressor gene, Mol. Cell. Biol., 25(18):7953-65 (2005).

* cited by examiner

*Primary Examiner* — Lianko G Garyu
(74) *Attorney, Agent, or Firm* — Marshall, Gerstein & Borun LLP

(57) ABSTRACT

The present disclosure relates to a novel recombinant BAF57 fusion protein and the use thereof as a composition capable of effectively preventing or treating inflammatory disease, immune-related disease or cancer.
The fusion protein provided in the present disclosure may be delivered into cells, bind to BAF155 or other BAF complex subunit, and act as a competitive inhibitor of BAF57 present in the cell, thereby lowering the expression level of BAF57 by a protein degradation mechanism, thereby effectively preventing, ameliorating or treating various diseases such as inflammatory disease, immune-related disease or cancer.

12 Claims, 17 Drawing Sheets

Specification includes a Sequence Listing.

[FIG. 1]
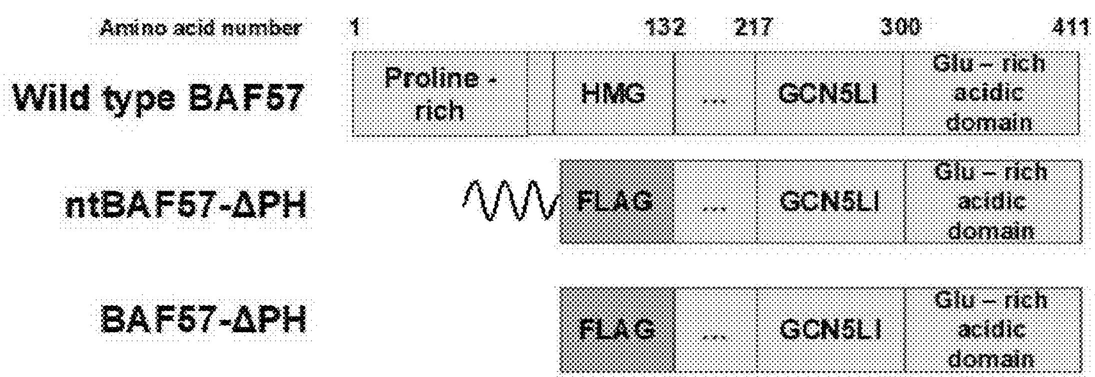

[FIG. 2]
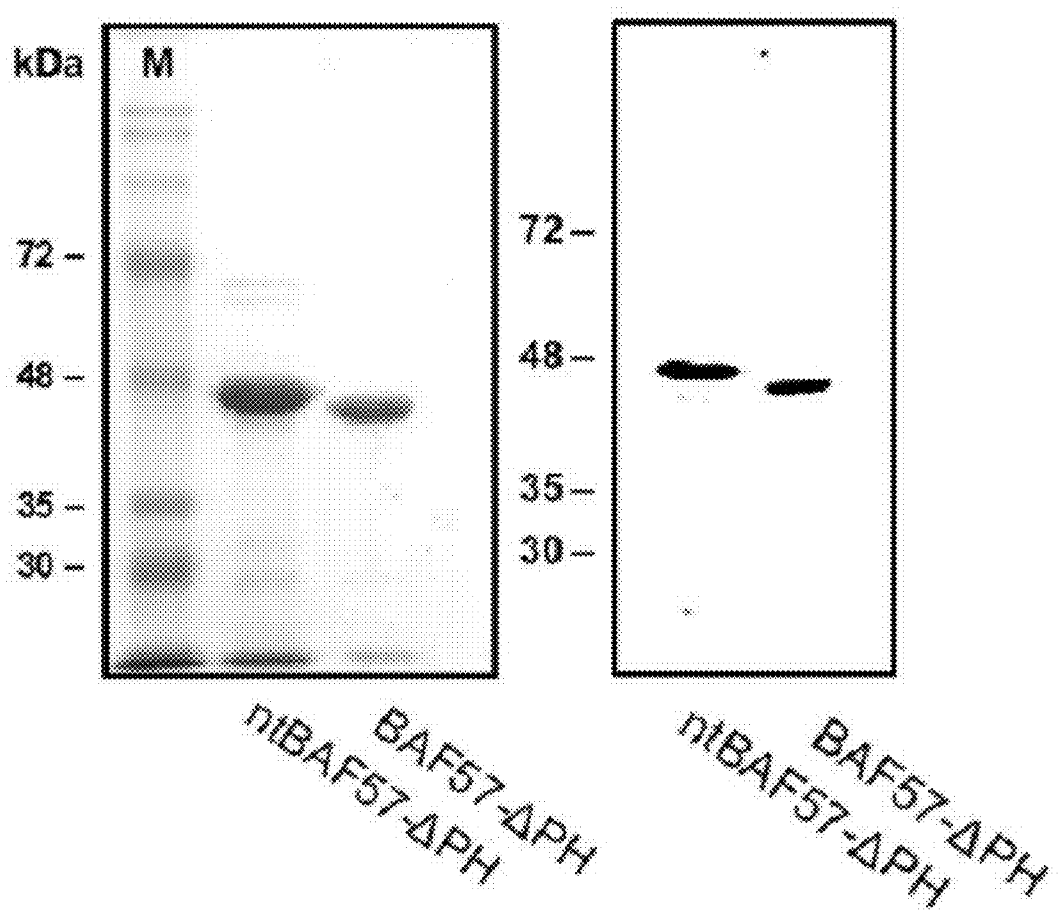

[FIG. 3]
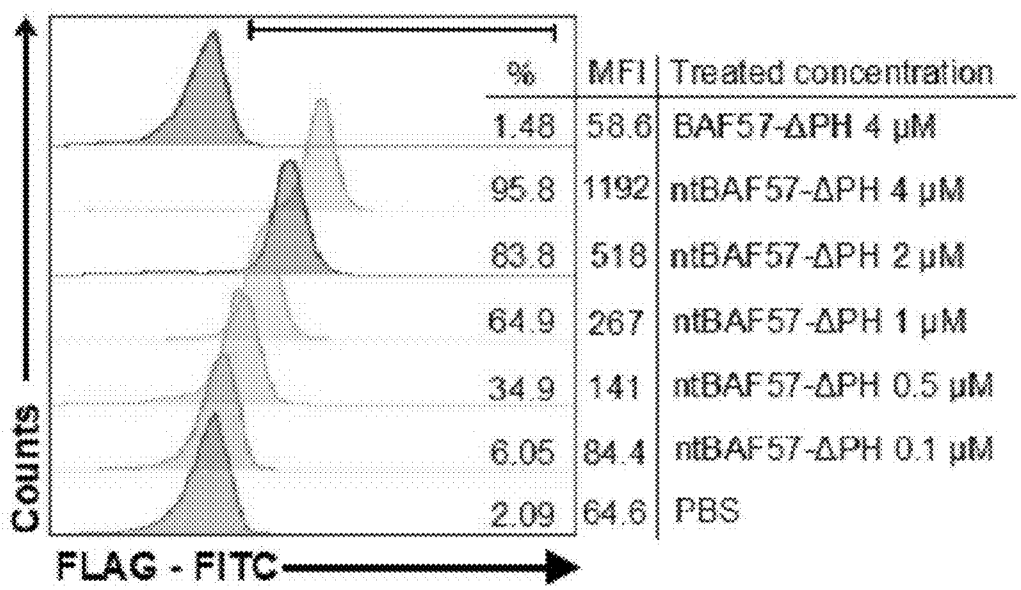
[FIG. 4]
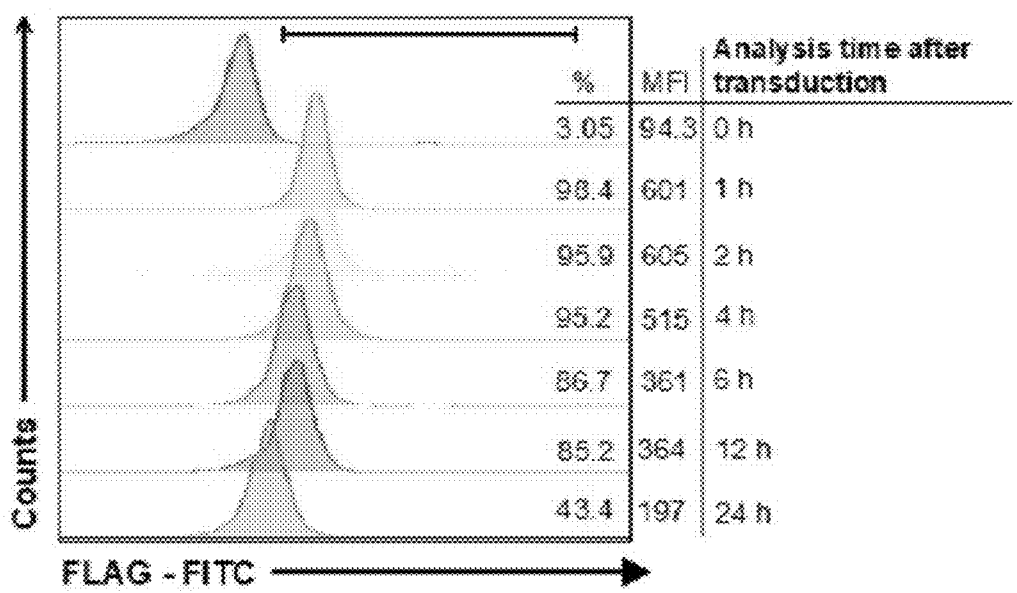

[FIG. 5]
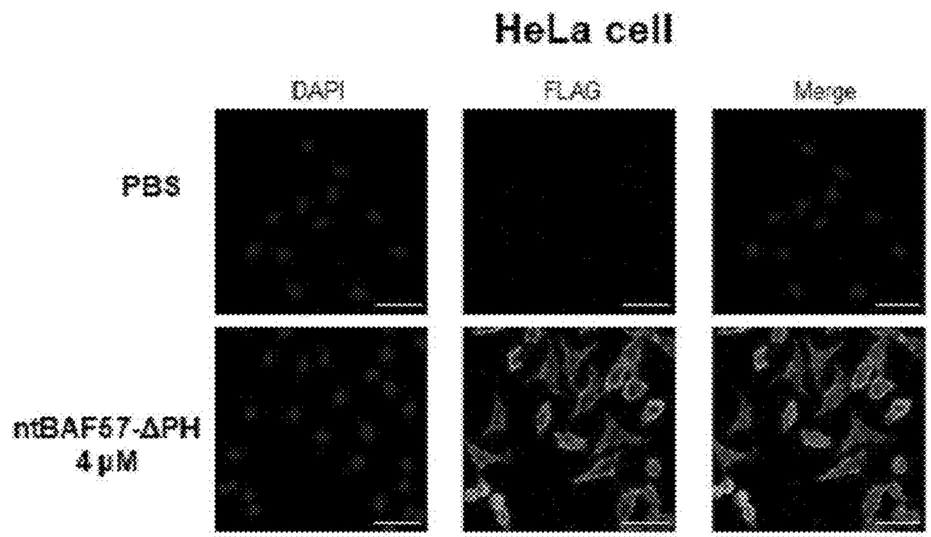
[FIG. 6]
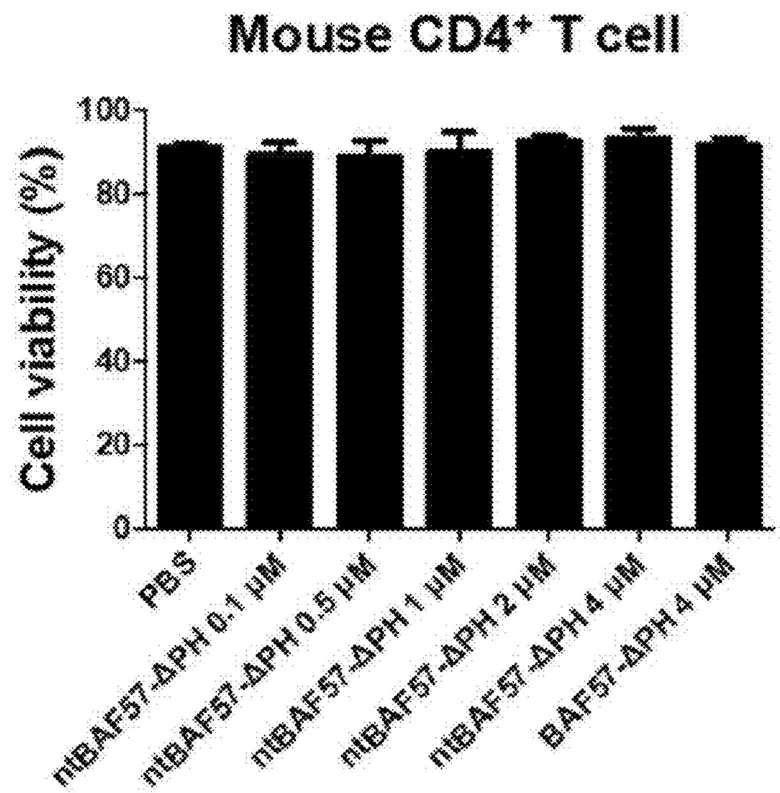

[FIG. 7]
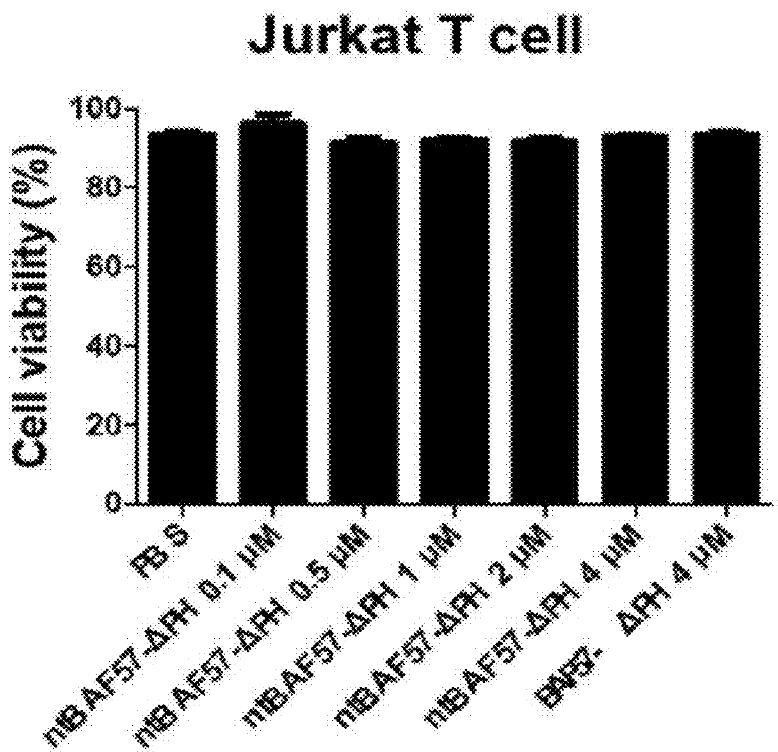
[FIG. 8]
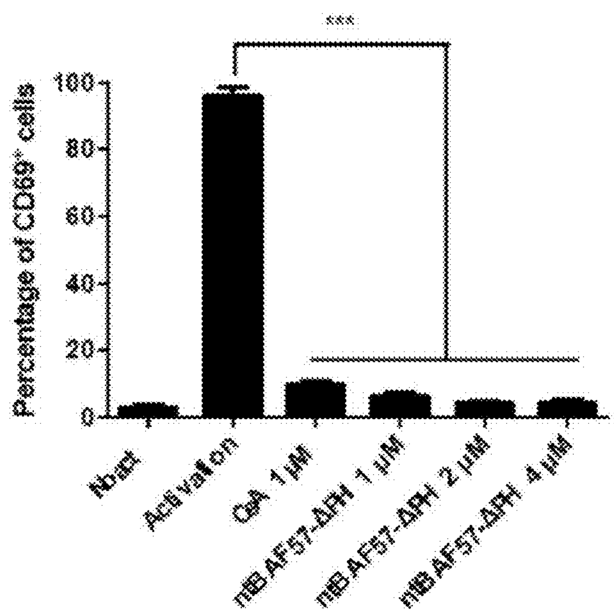

[FIG. 9]
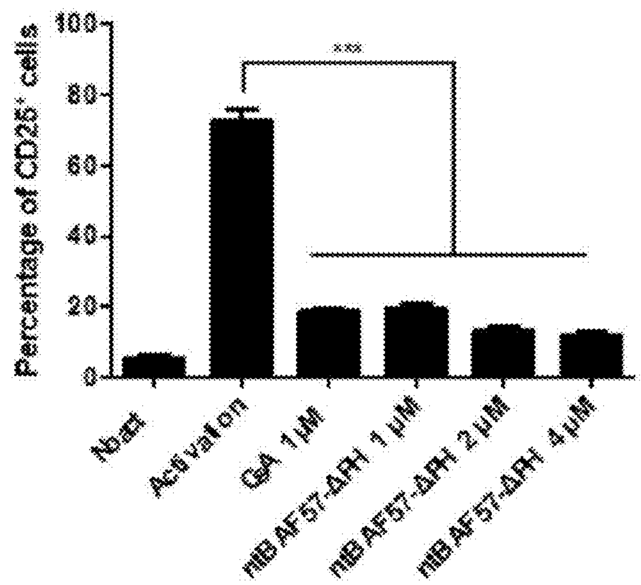
[FIG. 10]
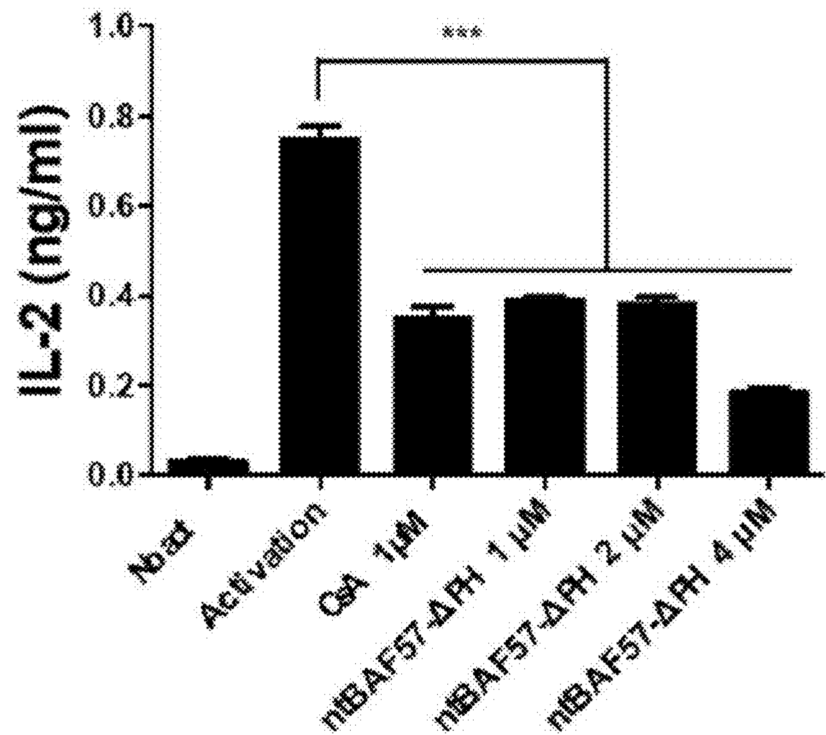

[FIG. 11]
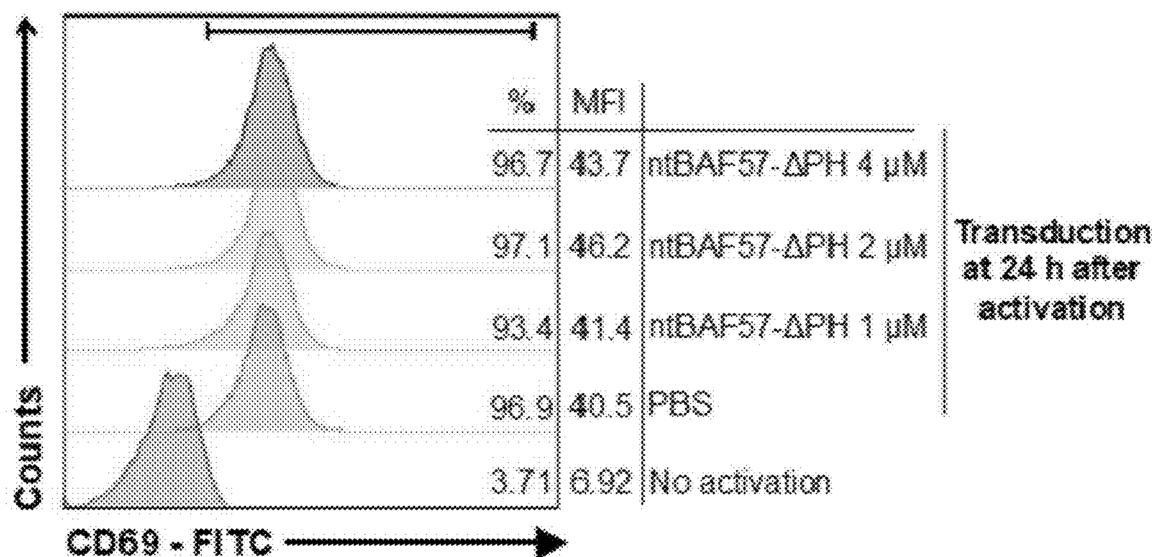
[FIG. 12]
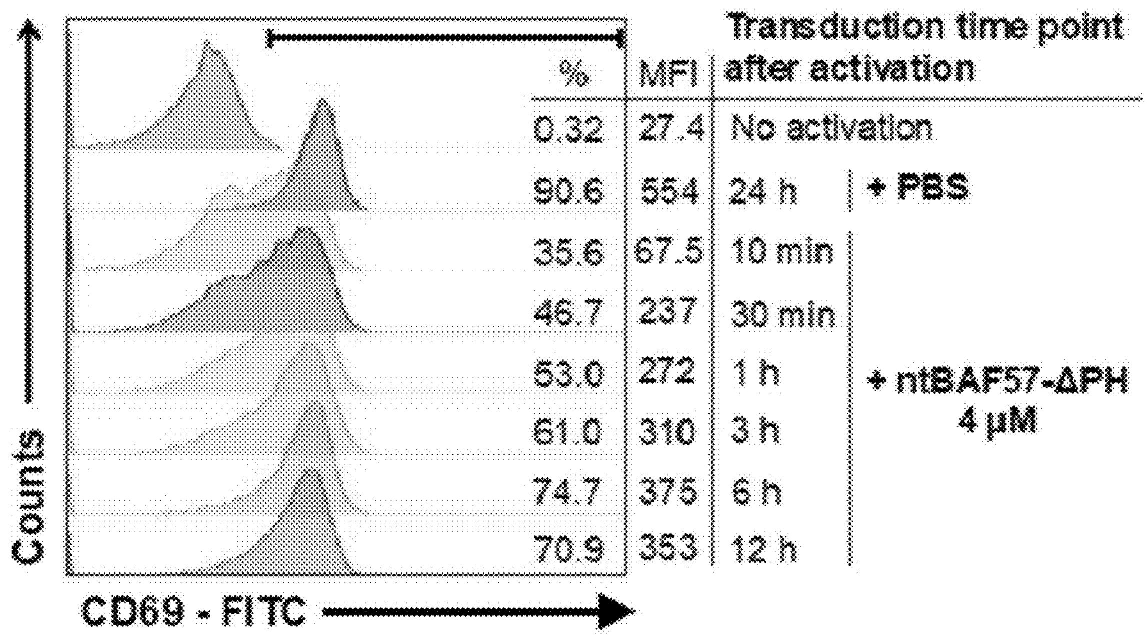

[FIG. 13]
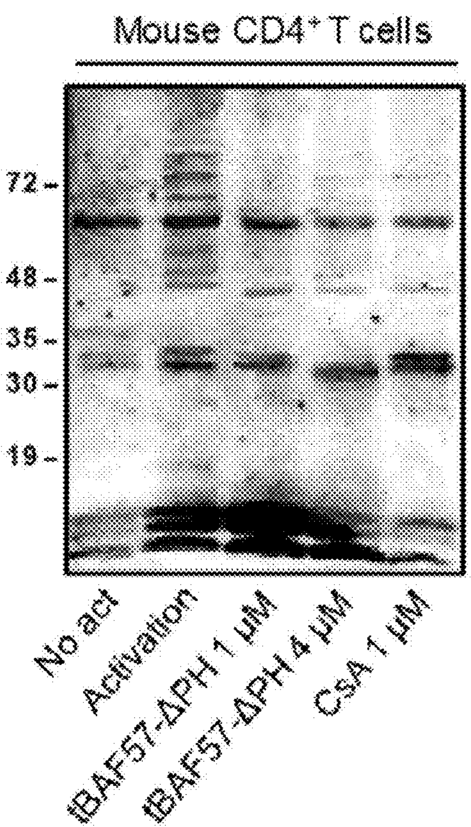
[FIG. 14]
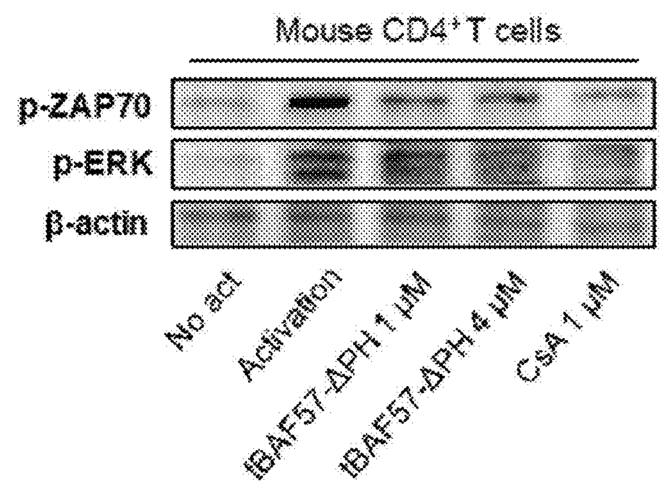

[FIG. 15]
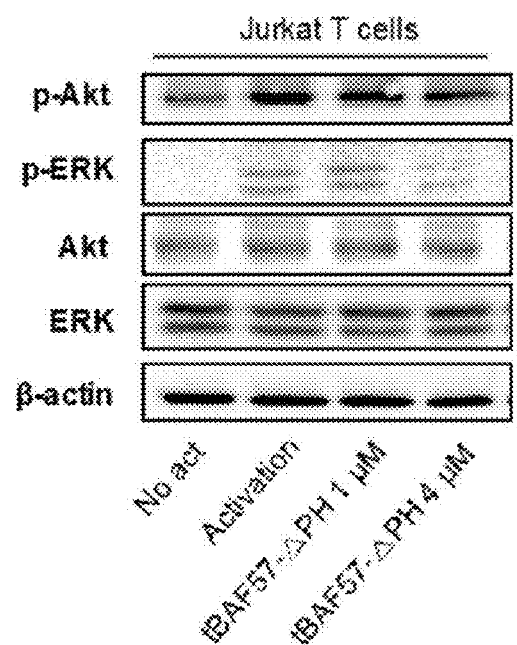
[FIG. 16]
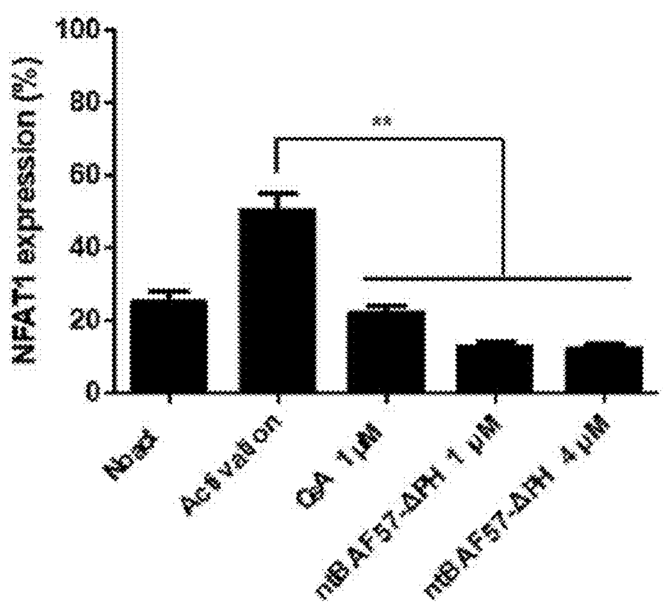

[FIG. 17]
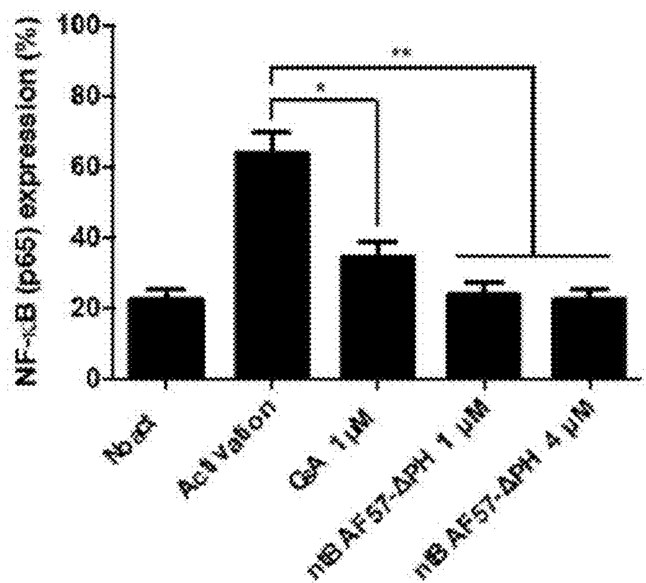
[FIG. 18]
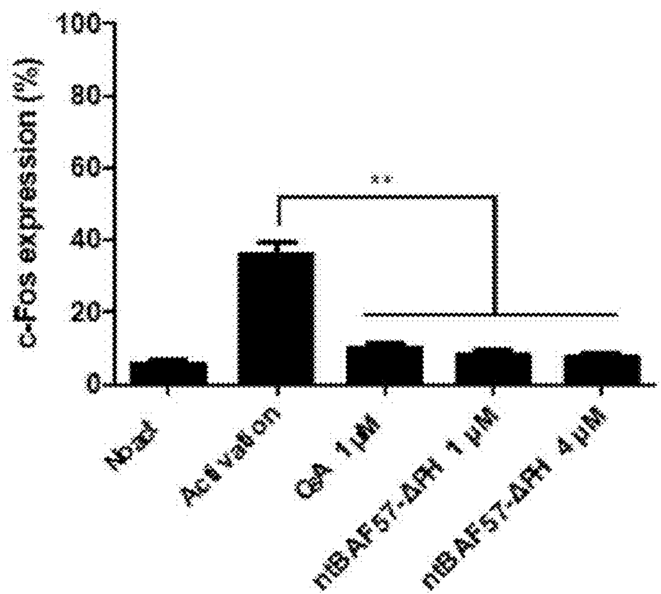

[FIG. 19]
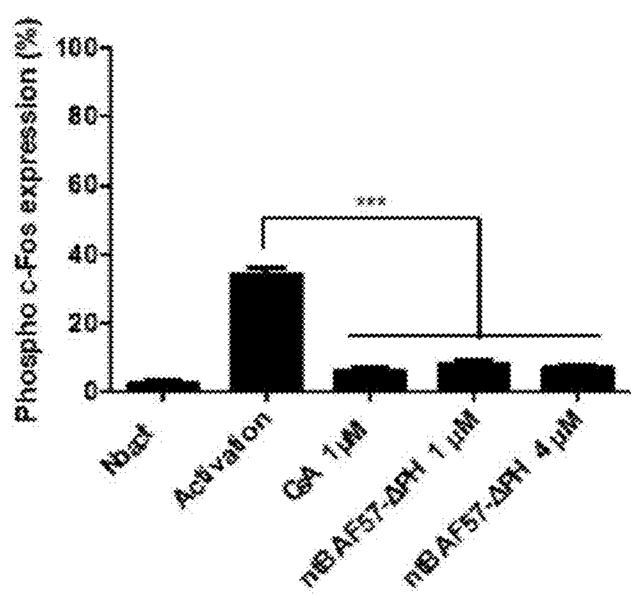
[FIG. 20]
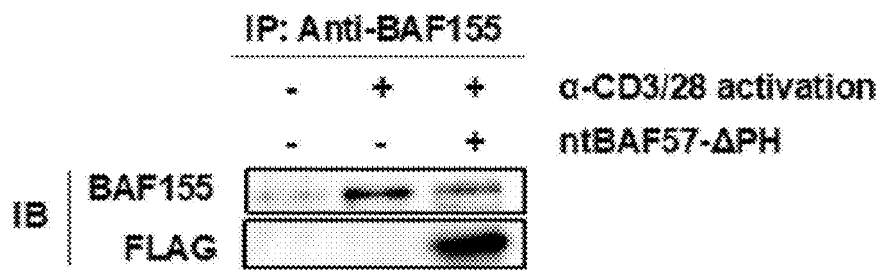

[FIG. 21]
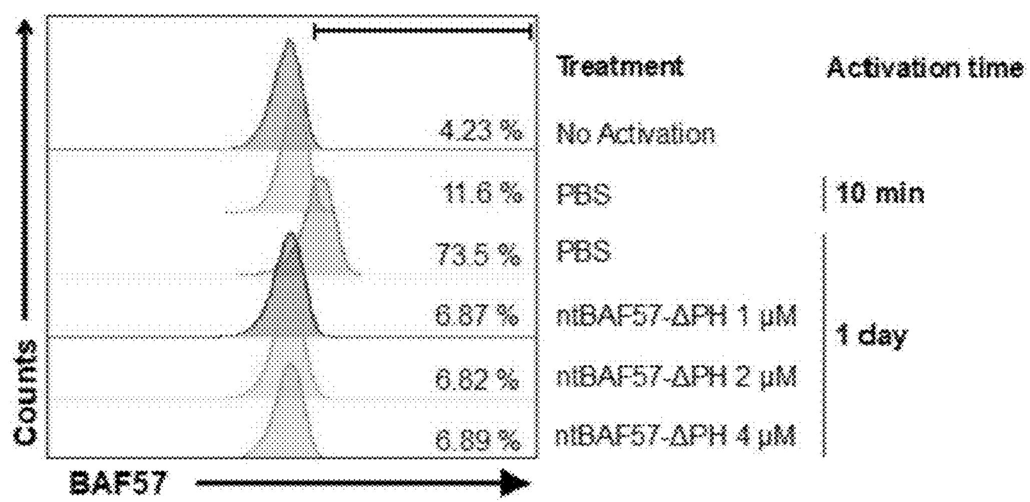
[FIG. 22]
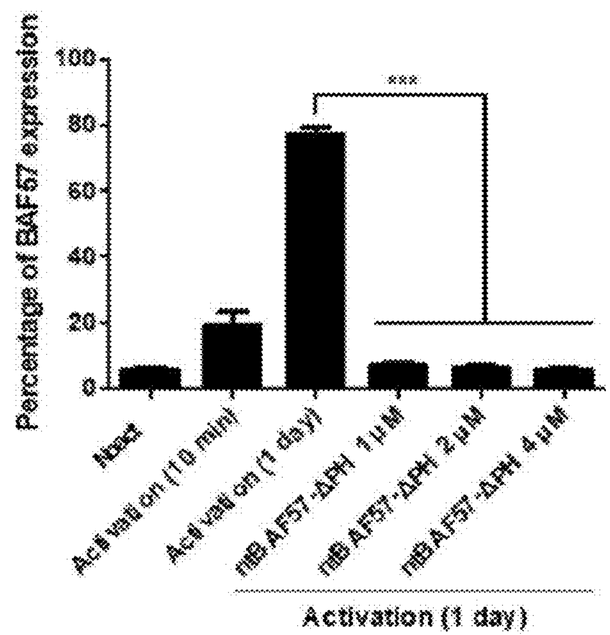

[FIG. 23]
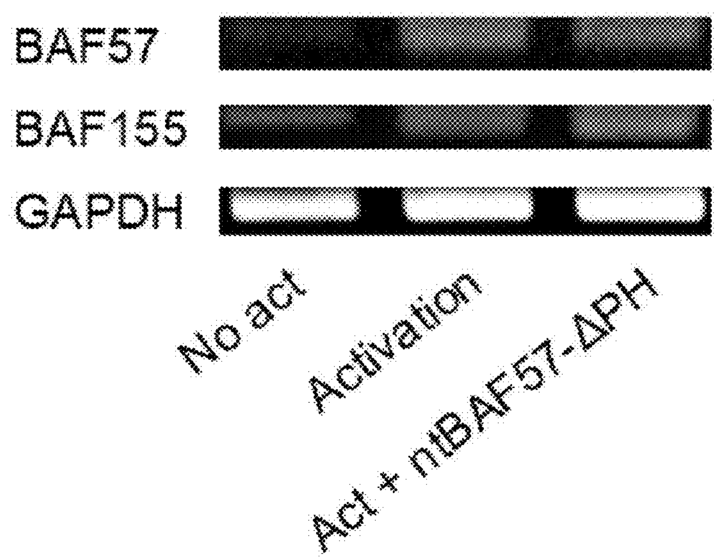
[FIG. 24]
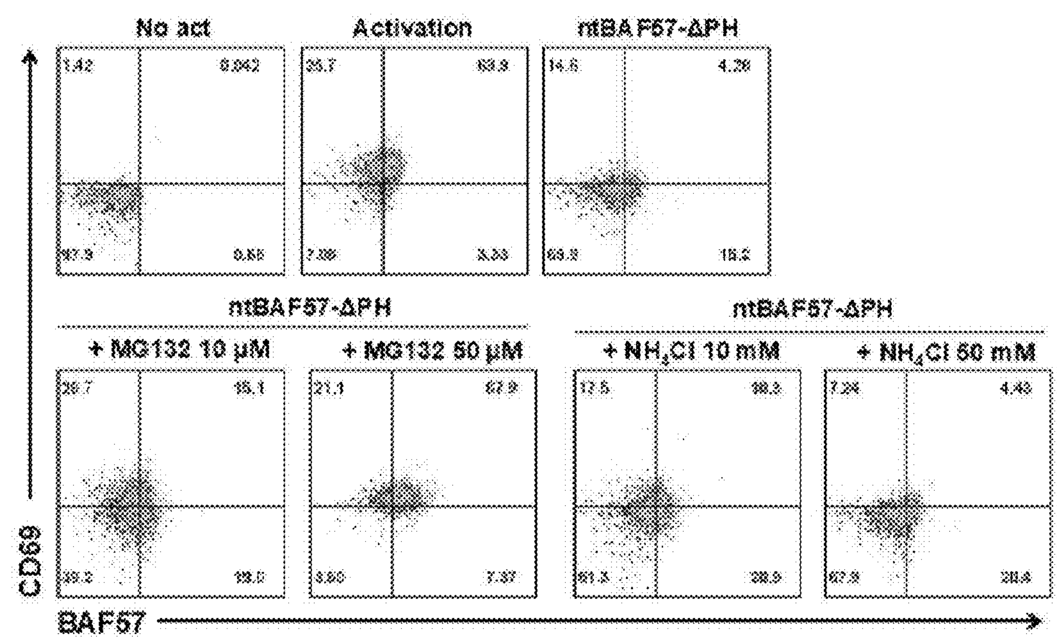

[FIG. 25]
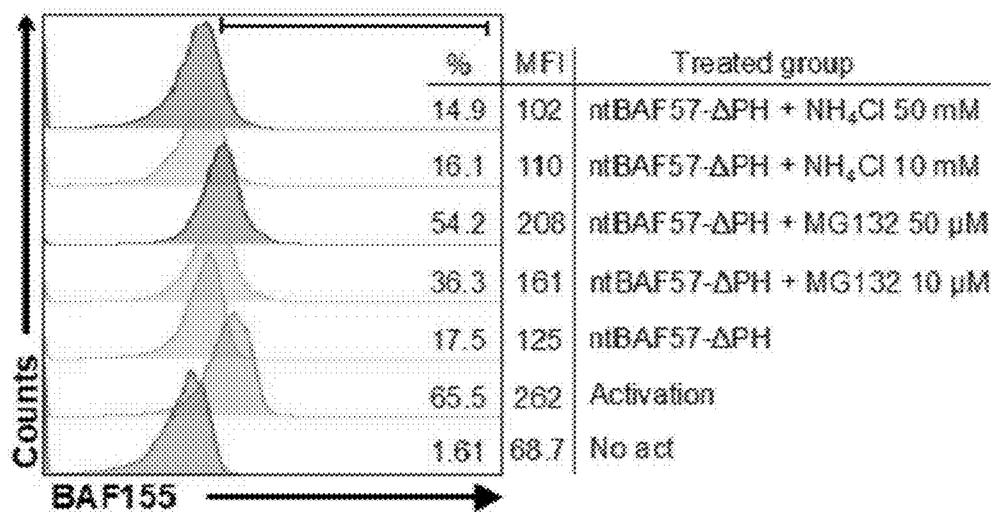
[FIG. 26]
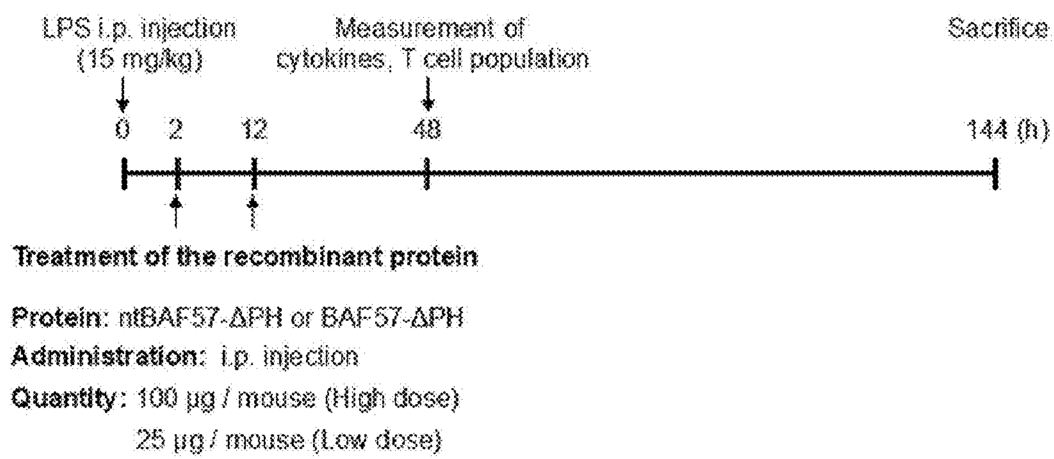

[FIG. 27]
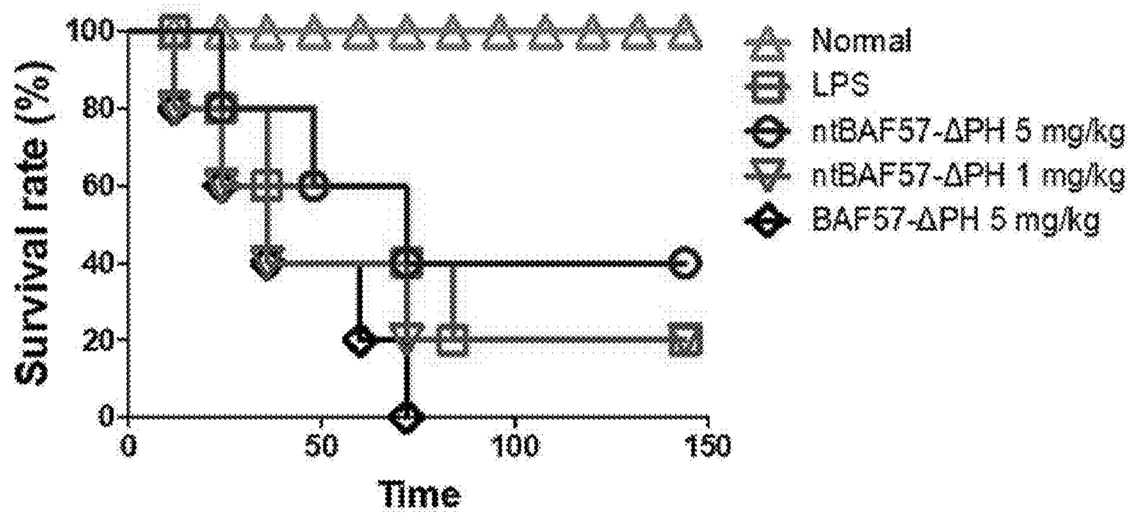
[FIG. 28]
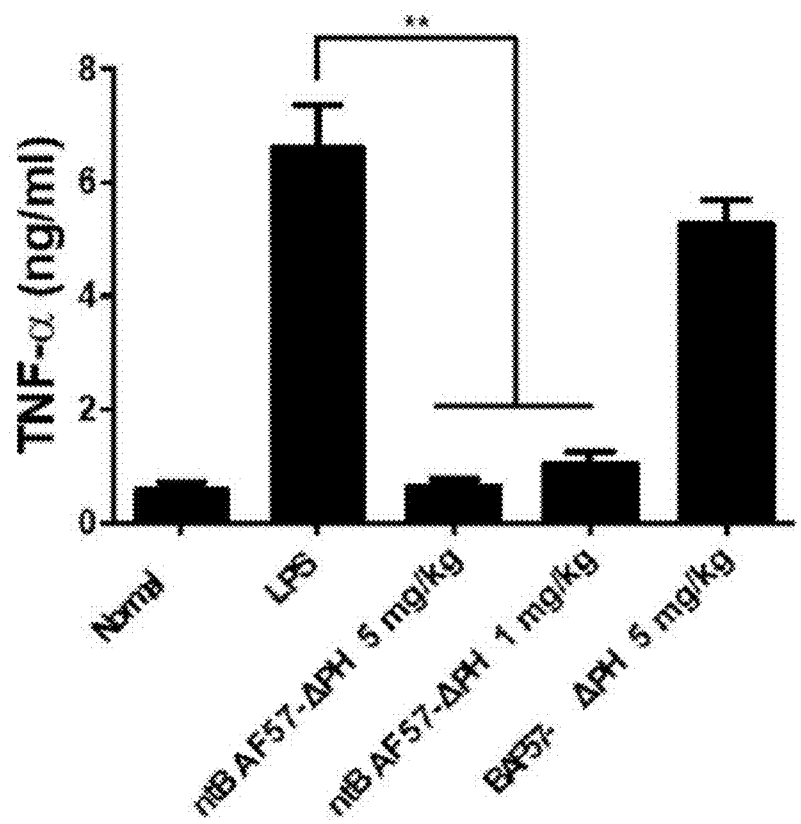

[FIG. 29]
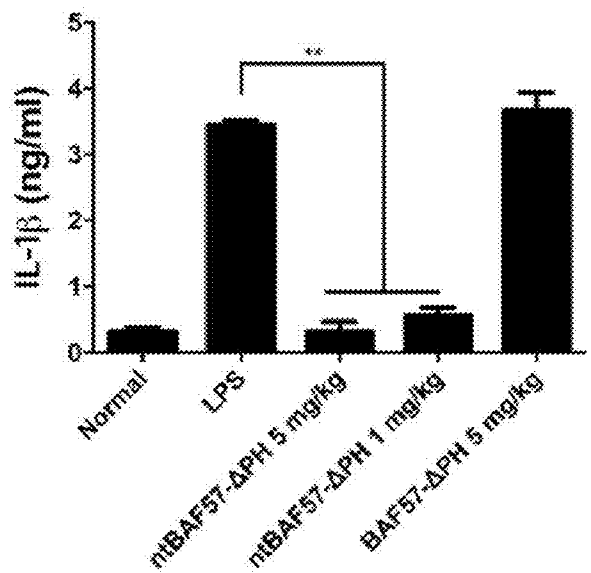
[FIG. 30]
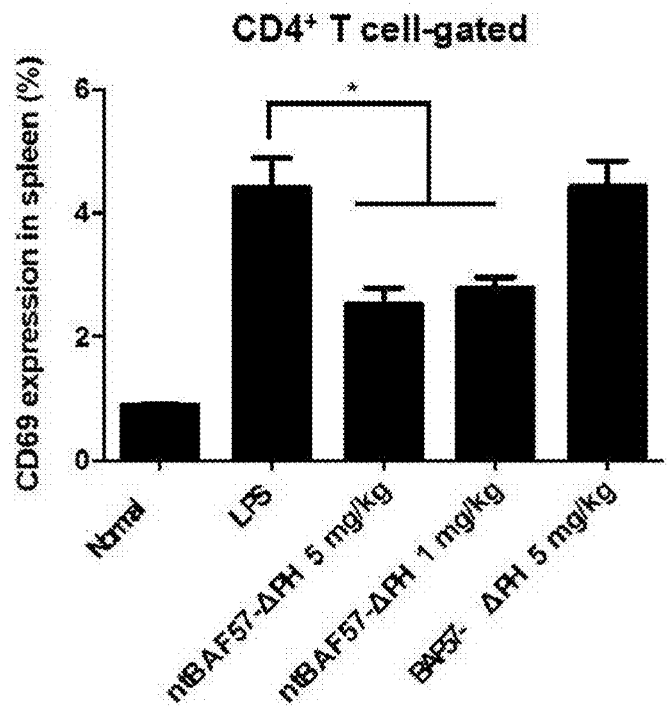

[FIG. 31]
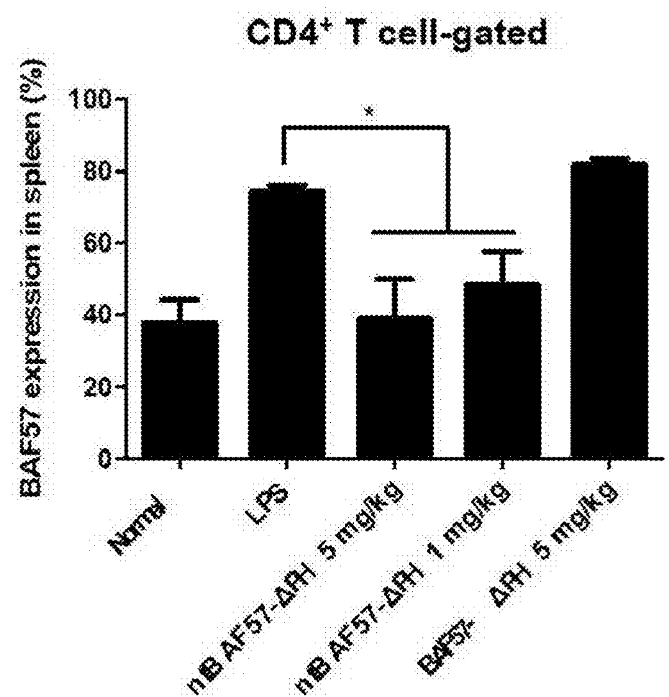

RECOMBINANT FUSION PROTEIN OF BAF57 AND USES THEREOF

CROSS-REFERENCE TO RELATED APPLICATION(S) AND INCORPORATION BY REFERENCE

This application claims priority to Korean Patent Application No(s). 10-2018-0172499, filed on Dec. 28, 2018, the disclosure of which is incorporated herein by reference in its entirety. Also incorporated by reference in its entirety is a computer-readable nucleotide/amino acid sequence listing submitted concurrently herewith and identified as follows: ASCII (text) file named "55125_SubSeqlisting.txt", 27,655 bytes, created on Apr. 1, 2020.

BACKGROUND

Technical Field

The present disclosure relates to a novel recombinant BAF57 fusion protein and the use thereof as a composition capable of effectively preventing or treating inflammatory disease, immune-related disease or cancer.

Description of the Related Art

Histones are basic proteins that are commonly found in the nucleus of eukaryotic cells, ranging from multicellular organisms including humans to unicellular organisms represented by fungi (mold and yeast) and ionically bind to genomic DNA. Histones usually consist of five components (H1, H2A, H2B, H3 and H4) and are highly similar across biological species. In the case of histone H4, for example, budding yeast histone H4 (full-length 102 amino acid sequence) and human histone H4 (full-length 102 amino acid sequence) are identical in 92% of the amino acid sequences and differ only in 8 residues. Among the natural proteins assumed to be present in several tens of thousands of organisms, histones are known to be proteins most highly preserved among eukaryotic species. Genomic DNA is folded with histones by ordered binding, and a complex of the both forms a basic structural unit called nucleosome. In addition, aggregation of the nucleosomes forms a chromosomal chromatin structure. Histones are subject to modifications, such as acetylation, methylation, phosphorylation, ubiquitination, SUMOylation and the like, at their N-terminal ends called histone tails, and maintain or specifically convert the chromatin structure, thereby controlling responses such as gene expression, DNA replication, DNA repair and the like, which occur on chromosomal DNA. Post-translational modification of histone is an epigenetic regulatory mechanism, and is considered essential for the genetic regulation of eukaryotic cells. Recent studies have revealed that chromatin remodeling factors such as SWI/SNF, RSC, NURF, NRD and the like, which encourage DNA access to transcription factors by modifying the nucleosome structure, histone acetyltransferases (HATs) that regulate the acetylation state of histones, and histone deacetylases (HDACs), act as important regulators (Korean Patent Application No. 10-2011-0081688).

Meanwhile, as protein domain structures that bind to acetylated lysine of histones, bromodomains are known. About 30 kinds of bromodomain-containing proteins are found in humans. Among these bromodomain-containing proteins, a BAF complex is one of various chromosome remodelers involved in a chromosome remodeling process known to be important for T-cell development and activation signal transduction, and this remodeler is known to play a role in modifying the chromosome using ATP. The BAF complex consists of several subunits. Among these subunits, BRG1, a protein that interacts with acetylated histones, is well known as a core protein of the SWI/SNF complex, a chromatin remodeling factor. Many studies on the role of BRG1 in T-cell development and activation signal transduction have been conducted. However, BAF57 (BRG1 or HBRM-associated factors 57) which is another subunit is not well known for its role in T cells.

SUMMARY

An object of the present disclosure is directed to a novel recombinant BAF57 fusion protein.

Another object of the present disclosure is directed to a composition capable of effectively preventing, ameliorating or treating inflammatory disease or immune-related disease using the recombinant BAF57 fusion protein.

Still another object of the present disclosure is directed to a composition capable of effectively preventing, ameliorating or treating cancer using the recombinant BAF57 fusion protein.

However, technical problems to be solved by the present disclosure are not limited to the above-mentioned problems, and other problems which are not mentioned will be clearly understood by those skilled in the art from the following description.

Hereinafter, various embodiments described herein will be described with reference to figures. In the following description, numerous specific details are set forth, such as specific configurations, compositions, and processes, etc., in order to provide a thorough understanding of the present disclosure. However, certain embodiments may be practiced without one or more of these specific details, or in combination with other known methods and configurations. In other instances, known processes and preparation techniques have not been described in particular detail in order to not unnecessarily obscure the present disclosure. Reference throughout this specification to "one embodiment" or "an embodiment" means that a particular feature, configuration, composition, or characteristic described in connection with the embodiment is included in at least one embodiment of the present disclosure. Thus, the appearances of the phrase "in one embodiment" or "an embodiment" in various places throughout this specification are not necessarily referring to the same embodiment of the present disclosure. Additionally, the particular features, configurations, compositions, or characteristics may be combined in any suitable manner in one or more embodiments.

Unless otherwise stated in the present specification, all the scientific and technical terms used in the present specification have the same meanings as commonly understood by those skilled in the technical field to which the present disclosure pertains.

According to one embodiment of the present disclosure, there is provided a fusion protein comprising: all or part of a BAF57 (BRG1 or HBRM-associated factors 57) protein; and a protein transduction domain.

In the present disclosure, all or part of the BAF57 protein may be derived from a mammal including humans, primates such as monkeys, rodents such as mice and rats, and the like.

In the present disclosure, the BAF57 protein may consist of the amino acid sequence represented by SEQ ID NO: 1, or may be encoded by the nucleotide sequence represented by SEQ ID NO: 2.

In addition, in the present disclosure, part of the BAF57 protein means any one fragment of the BAF57 protein, and may include, without limitation, any polypeptide fragment that may bind to BAF155 or other BAF complex subunit and act as a competitive inhibitor of BAF57 present in cells, but is not particularly limited thereto.

In a preferred example of the present disclosure, part of the BAF57 protein may be a polypeptide fragment obtained by removing an HMG domain, which is a DNA-binding domain, and a proline-rich domain which is an N-terminal portion, from the BAF57 protein. More preferably, part of the BAF57 protein may consist of the amino acid sequence represented by SEQ ID NO: 3, or may be encoded by the nucleotide sequence represented by SEQ ID NO: 4.

In the present disclosure, the protein transduction domain refers to a strongly hydrophobic short peptide consisting of 7 to 50 amino acids, which is a domain capable of intracellularly delivering not only a protein having a molecular weight of 120 kDa or more, but also DNA or RNA. For example, the protein transduction domain may be selected from the group consisting of Hph-1, Mph-1, Sim-2, Tat, VP22, Antp (antennapedia), Pep-1 (peptide-1), PTD-5 (protein transduction domain-5), MAP, K-FGF, penetratin, transportan, polyarginine, 11R, 7R and CTP (cytoplamic transduction peptide), but is not limited thereto. Here, “11R” and “7R” mean peptides consisting of 11 arginines and 7 arginines, respectively.

In one example of the present disclosure, the protein transduction domain may be Hph-1. Preferably, it may consist of the amino acid sequence represented by SEQ ID NO: 5, or may be encoded by the nucleotide sequence represented by SEQ ID NO: 6.

In one example of the present disclosure, the protein transduction domain may be linked to the N-terminus or C-terminus of all or part of the BAF57 protein. Preferably it may be linked to the N-terminus.

The fusion protein of the present disclosure may further comprise a tag for separation and purification.

In the present disclosure, the tag may be at least one of an affinity tag and an epitope tag.

In one example of the present disclosure, the affinity tag may be a histidine tag, glutathione S-transferase (GST), Intein, chitin binding protein (CBP), maltose binding protein (MBP), an avidin tag or a streptavidin tag, but is not limited thereto.

In one example of the present disclosure, the epitope tag may be a FLAG tag, a Myc tag, a V5 tag, an HA (hemagglutinin) tag, a Spot tag or an NE tag, but is not limited thereto.

In one example of the present disclosure, the tag may be a FLAG tag. Preferably, it may consist of the amino acid sequence represented by SEQ ID NO: 7, or may be encoded by the nucleotide sequence represented by SEQ ID NO: 8.

In one example of the present disclosure, the tag may be linked to N-terminus or C-terminus of all or part of the BAF57 protein. Preferably, it may be linked to the N-terminus.

In one preferred example of the present disclosure, the fusion protein may be composed of the amino acid sequence represented by any one of SEQ ID NOs: 9 to 11.

The fusion protein of the present disclosure may be delivered intracellularly, bind to BAF155 or other BAF complex subunit, and act as a competitive inhibitor of BAF57 present in the cell, thereby lowering the expression level of BAF57 by a protein degradation mechanism and also inhibiting the expression of BAF155 from being increased.

According to another embodiment of the present disclosure, there is provided a nucleic acid molecule encoding the fusion protein provided in the present disclosure.

The nucleic acid molecule of the present disclosure includes any nucleic acid molecule obtained by translating the amino acid sequence of the fusion protein provided in the present disclosure into a polynucleotide sequence as known to those skilled in the art. Therefore, various polynucleotide sequences can be produced by an open reading frame (ORF), and are all also included in the nucleic acid molecule of the present disclosure.

In one preferred example of the present disclosure, the nucleic acid molecule may consist of the nucleotide sequence represented by any one of SEQ ID NOs: 12 to 14.

According to still another embodiment of the present disclosure, there is provided an expression vector in which the nucleic acid molecule provided in the present disclosure is inserted.

In the present disclosure, the “vector” is the nucleic acid molecule capable of transporting another nucleic acid to which any nucleic acid molecule has been linked. One type of vector is a “plasmid,” which refers to a circular double-stranded DNA loop into which additional DNA segment may be ligated. Another type of vector is a phage vector. Another type of vector is a viral vector, wherein additional DNA segments may be ligated into the viral genome. Certain vectors are capable of autonomous replication, in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as “recombinant expression vectors” (or simply, “expression vectors”). In general expression vectors of utility in recombinant DNA techniques are often in the form of plasmids. In the present specification, “plasmid” and “vector” may be used interchangeably as the plasmid is the most commonly used form of vector.

In a specific example of the present disclosure, the expression vector may be selected from the group consisting of a commercially widely available pCDNA vector, F, R1, RP1, Col, pBR322, ToL, Ti vector; cosmids; phages such as lambda, lambdoid, M13, Mu, p1, P22, Qu, T-even, T2, T3, T7, etc.; and plant viruse, but is not limited thereto. Any of expression vectors known to those skilled in the art may be used in the present disclosure, and the choice of the expression vector is dependent on the nature of the host cell of choice. Introduction of the vector into host cells can be effected by, but not limited to, calcium phosphate transfection, virus infection, DEAE-dextran mediated transfection, lipofectamin transfection or electroporation, and any person skilled in the art may select and use an introduction method suitable for the expression vector and host cell used. Preferably, the vector contains one or more selection markers, but is not limited thereto, and a vector containing no selection marker may also be used to determine whether a product would be produced. The choice of the selection markers may depend on the host cells of choice, and the present disclosure is not limited thereto as the choice is performed using a method already known to those skilled in the art.

To facilitate purification of the nucleic acid molecule of the present disclosure, a tag sequence may be inserted into and fused to the expression vector.

In the present disclosure, the tag may be at least one of an affinity tag and an epitope tag.

In one example of the present disclosure, the affinity tag may be a histidine tag, glutathione S-transferase (GST), Intein, chitin binding protein (CBP), maltose binding protein (MBP), an avidin tag or a streptavidin tag, but is not limited thereto.

In one example of the present disclosure, the epitope tag may be a FLAG tag, a Myc tag, a V5 tag, an HA (hemagglutinin) tag, a Spot tag or an NE tag, but is not limited thereto.

However, the tag in the present disclosure is not limited to the above-listed types, and tags known to those in the art, which facilitate purification, may all be used in the present disclosure.

According to yet another embodiment of the present disclosure, there is provided a host cell transformed with the expression vector provided in the present disclosure.

In the present disclosure, the "host cell" includes an individual cell or cell culture that can be or has been a recipient for a vector(s) for incorporation of polypeptide inserts. Host cells include progeny of a single host cell, and the progeny may not necessarily be completely identical (in morphology or in genomic DNA complement) to the original parent cell due to natural, accidental, or deliberate mutation. The host cell includes cells transfected in vivo with a polypeptide(s) of the present disclosure.

In the present disclosure, the host cell may include but is not limited to, cells of mammalian, plant, insect, fungal or cellular origin. For example, the host cell may include, but is not limited to, bacteria cells such as *E. coli, Streptomyces, Salmonella typhimurium*, etc.; yeast cells; fungal cells such as *Pichia pastoris*, etc.; insect cells such as *Drosophila, Spodoptera* Sf9 cells, etc.; animal cells such as CHO (Chinese hamster ovary cells), SP2/0 (mouse myeloma cells), human lymphoblastoids, COS, NSO (mouse myeloma cells), 293T, Bowes melanoma cells, HT-1080, BHK (baby hamster kidney cells), HEK (human embryonic kidney cells), or PERC.6 (human embryonic retina cells); or plant cells. In addition, all types of cells available as host cells as known those in the art may also be used in the present disclosure.

According to yet another embodiment of the present disclosure, there is provided a pharmaceutical composition for preventing or treating inflammatory disease or immune-related disease comprising, as an active ingredient, the fusion protein provided in the present disclosure.

The fusion protein of the present disclosure may be delivered intracellularly, bind to BAF155 or other BAF complex subunit, and act as a competitive inhibitor of BAF57 present in the cell, thereby lowering the expression level of BAF57 by a protein degradation mechanism and also inhibiting the expression of BAF155 from being increased. In addition, the fusion protein of the present disclosure is capable of effectively preventing, ameliorating or treating inflammatory disease and immune-related disease by inhibiting activation of T cells and lowering the expression level of inflammatory cytokines.

In the present disclosure, the "inflammatory disease" refers to a disease which is caused by inflammatory inducers (inflammatory cytokines), such as TNF-α, IL-1, IL-6, prostaglandin, leukotriene or NO, which are secreted from immune cells such as macrophages, by excessive stimulation of the immune system due to harmful stimuli such as inflammation-inducing factors or irradiation. In the present disclosure, examples of the inflammatory disease include, but are not limited to, asthma, eczema, psoriasis, allergy, rheumatoid arthritis, psoriatic arthritis, atopic dermatitis, acne, atopic rhinitis, pulmonary inflammation, allergic dermatitis, chronic sinusitis, contact dermatitis, seborrheic dermatitis, gastritis, gout, gout arthritis, ulcer, chronic bronchitis, Crohn's disease, ulcerative colitis, ankylosing spondylitis, sepsis, angiitis, bursitis, lupus, rheumatic polymyalgia, temporal arteritis, multiple sclerosis, solid cancer, Alzheimer's disease, arteriosclerosis, obesity, or viral infection.

In the present disclosure, the "immune-related disease" is a disease caused by excessive activation and expression of various types of immune cells and inflammatory cells, and examples thereof include, but are not limited to, autoimmune diseases; graft-versus-host diseases; or cell, tissue or organ transplant rejection disease.

In addition, in the present disclosure, the term "autoimmune disease" refers to a disease caused by a process in which a problem occurs in inducing or maintaining self-tolerance and an immune response to a self-antigen occurs, thereby attacking the own tissue. The term "self-tolerance" refers to immunologic unresponsiveness that does not react harmful to an antigenic substance constituting self. In the present disclosure, examples of the autoimmune disease include, but are not limited to, rheumatoid arthritis, systemic scleroderma, systemic lupus erythematosus, atopic dermatitis, psoriasis, alopecia areata, asthma, Crohn's disease, Behcet's disease, Sjogren's syndrome, Gilliam-Barre syndrome, thyroiditis, Hashimoto's thyroiditis, multiple sclerosis, multiple myositis, ankylosing spondylitis, fibromyalgia, nodular polyarteritis, insulin-dependent diabetes, experimental autoimmune encephalomyelitis, experimental autoimmune arthritis, myasthenia gravis, an experimental form of uveitis, primary myxedema, thyroidism, pernicious anemia, autoimmune atrophic gastritis, Addison's disease, early menopause, male infertility, pediatric diabetes, Goodpasture syndrome, pemphigus vulgaris, pemphigoid, sympathetic ophthalmitis, lens-induced uveitis, autoimmune hemolytic anemia, idiopathic leukopenia, primary bile duct sclerosis, chronic active hepatitis Hbs-ve, potential cirrhosis, ulcerative colitis, scleroderma, Wegener's granulomatosis, polymyositis/skin myositis, or discoid LE.

According to yet another embodiment of the present disclosure, there is provided a pharmaceutical composition for preventing or treating cancer comprising, as an active ingredient, the fusion protein provided in the present disclosure.

In general, it is known that BAF57 plays an important role in the gene expression of estrogen receptor and androgen receptor, which play an important role in the development of cancers such as breast cancer and prostate cancer (THE JOURNAL OF BIOLOGICAL CHEMISTRY VOL. 281, NO. 32, pp. 22656-22664, Aug. 11, 2006; MOLECULAR AND CELLULAR BIOLOGY, March 2005, p. 2200-2215; Cancer Res 2008; 68: (12). Jun. 15, 2008). In addition, it is known that BAF155 activates cancer stem cells such as liver cancer cells (Nature Communications volume 7, Article number: 13608 (2016)).

However, the fusion protein of the present disclosure may be delivered into cells, bind to BAF155 or other BAF complex subunit, and act as a competitive inhibitor of BAF57 present in the cells, thereby lowering the expression level of BAF57 by a protein degradation mechanism and also inhibiting the expression of BAF155 from being increased. Therefore, the use of the fusion protein of the present disclosure is capable of effectively preventing, ameliorating or treating cancer.

In the present disclosure, the cancer refers to or describes the physiological condition that is typically characterized by unregulated cell growth. According to the site of occurrence, the cancer may be ovarian cancer, colorectal cancer, pancreatic cancer, gastric cancer, liver cancer, breast cancer, cervical cancer, thyroid cancer, parathyroid cancer, lung cancer, non-small cell lung cancer, prostate cancer, gallbladder cancer, biliary tract cancer, non-Hodgkin's lymphoma, Hodgkin's lymphoma, blood cancer, bladder cancer, kidney cancer, melanoma, colon cancer, bone cancer, skin cancer, head cancer, uterine cancer, rectal cancer, brain cancer, perianal cancer, fallopian tube carcinoma, endometrial carcinoma, vaginal cancer, vulvar carcinoma, esophageal cancer, small intestine cancer, endocrine adenocarcinoma, adrenal cancer, soft tissue sarcoma, urethral cancer, penile cancer, ureter cancer, renal cell carcinoma, renal pelvic carcinoma, central nervous system (CNS) tumor, primary CNS lymphoma, spinal cord tumor, brainstem glioma, or pituitary adenoma, but are not limited to.

The composition of the present disclosure may be co-administered with other anticancer agent, thereby exhibiting an adjuvant effect of enhancing the anticancer effect of the anticancer agent. As the anticancer agent, there may be used one or more selected from the group consisting of nitrogen mustard, imatinib, oxaliplatin, rituximab, erlotinib, neratinib, lapatinib, gefitinib, vandetanib, nilotinib, semaxanib, bosutinib, axitinib, masitinib, cediranib, lestaurtinib, trastuzumab, gefitinib, bortezomib, sunitinib, pazopanib, toceranib, nintedanib, regorafenib, semaxanib, tivozanib, ponatinib, cabozantinib, carboplatin, sorafenib, lenvatinib, bevacizumab, cisplatin, cetuximab, viscum album, asparaginase, tretinoin, hydroxycarbamide, dasatinib, estramustine, gemtuzumab ozogamicin, ibritumomab tiuxetan, heptaplatin, methyl aminolevulinic acid, amsacrine, alemtuzumab, procarbazine, alprostadil, holmium nitrate-chitosan, gemcitabine, doxifluridine, pemetrexed, tegafur, capecitabine, gimeracil, oteracil, azacitidine, methotrexate, uracil, cytarabine, 5-fluorouracil, fludarabine, enocitabine, flutamide, capecitabine, decitabine, mercaptopurine, thioguanine, cladribine, carmofur, raltitrexed, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, peplomycin, temsirolimus, temozolomide, busulfan, ifosfamide, cyclophosphamide, melphalan, altretamine, dacarbazine, thiotepa, nimustine, chlorambucil, mitolactol, leucovorin, tretinoin, exemestane, aminogluthetimide, anagrelide, olaparib, navelbine, fadrozole, tamoxifen, toremifene, testolactone, anastrozole, letrozole, vorozole, bicalutamide, lomustine, vorinostat, entinostat and carmustine, but is not limited thereto.

Meanwhile, in the present disclosure, "preventing" may include, without limitation, any action that blocks, inhibits or delays symptoms of a disease using the pharmaceutical composition of the present disclosure.

In addition, in the present disclosure, "treating" may include, without limitation, any action that alleviates or beneficially changes symptoms of a disease using the pharmaceutical composition of the present disclosure.

In the present disclosure, the pharmaceutical composition may be in the form of capsule, tablet, granule, injection solution, ointment, powder or beverage, and the pharmaceutical composition may be intended for humans.

In the present disclosure, the pharmaceutical composition may be formulated and used as oral formulations, such as powders, granules, capsules, tablets or aqueous suspensions, skin external preparations, suppositories, and sterile injectable solutions, according to the respective conventional methods, but is not limited thereto. The pharmaceutical composition of the present disclosure may comprise a pharmaceutically acceptable carrier. For oral administration, the pharmaceutically acceptable carrier may include a binder, a lubricant, a disintegrant, an excipient, a solubilizing agent, a dispersing agent, a stabilizing agent, a suspending agent, a coloring agent, fragrance, etc., and for injection, the pharmaceutically acceptable carrier may include a buffer, a preservative, a pain killing agent, a solubilizing agent, an isotonic agent, a stabilizing agent, etc., and for topical administration, the pharmaceutically acceptable carrier may include a base, an excipient, a lubricant, a preservative, etc. The formulation of the pharmaceutical composition of the present disclosure may be prepared in various forms by mixing with the pharmaceutically acceptable carrier as described above. For example, for oral administration, the pharmaceutical composition may be prepared in the form of tablet, troche, capsule, elixir, suspension, syrup, wafer, etc., and for injection, the pharmaceutical composition may be prepared in the form of unit dosage ampoule or multiple-dose container. In addition, the pharmaceutical composition may be prepared as a solution, suspension, tablet, capsule or sustained-release formulation.

Meanwhile, examples of carriers, excipients and diluents suitable for formulation may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate or mineral oil. In addition, the pharmaceutical composition may further comprise a filler, an anti-coagulant, a lubricant, a wetting agent, fragrance, an emulsifier, a preservative, etc.

The routes of administration of the pharmaceutical composition of the present disclosure include, but are not limited to, oral, intravenous, intramuscular, intra-arterial, intra-marrow, intradural, intracardiac, transdermal, subcutaneous, intraperitoneal, intranasal, intestinal, local, sublingual or intrarectal routes. Oral or parenteral administration is preferred.

In the present disclosure, "parenteral" includes subcutaneous, transdermal, intravenous, intramuscular, intra-articular, intra-synovial, intrasternal, intradural, intra-lesional and intra-cranial injection or infusion techniques. The pharmaceutical composition of the present disclosure may also be formulated as suppositories for intrarectal administration.

The dose of the pharmaceutical composition of the present disclosure may vary depending on various factors, including the activity of a particular compound used, the patient's age, weight, general health condition, sex, diet, the duration of administration, the route of administration, excretion rate, drugs used in combination with the composition, or the severity of a particular disease to be treated. The dose of the pharmaceutical composition varies depending on the patient's condition and body weight, the severity of the disease, the form of drug, and the route and duration of administration, but may be suitably selected by a person skilled in the art. The pharmaceutical composition may be administered at a dose of 0.0001 to 50 mg/kg/day or 0.001 to 50 mg/kg/day. The pharmaceutical composition may be administered once or several times a day. The dose is not intended to limit the scope of the present disclosure in any way. The pharmaceutical composition according to the present disclosure may be formulated as pills, sugar-coated tablets, capsules, liquids, gels, syrups, slurries, or suspensions.

According to yet another embodiment of the present disclosure, there is provided a method for preventing or treating inflammatory disease or immune-related disease comprising a step of administering to a subject a pharmaceutically effective amount of any one or more of: the fusion protein according to the present disclosure; the expression vector; and the host cell.

In one embodiment of the present disclosure, there is provided a method for preventing or treating inflammatory disease or immune-related disease comprising a step of administering to a subject a pharmaceutically effective amount of the fusion protein according to the present disclosure.

In the present disclosure, the “subject” refers to a subject suspected of having inflammatory disease and immune-related disease. The subject suspected of having inflammatory disease and immune-related disease refers to mammals, including humans, rats, and domestic animals, that have or are at risk of developing the disease, but the subject includes, without limitation, subjects that may be treated with either the fusion protein provided in the present disclosure or an antibody-drug conjugate.

In the present disclosure, the method comprises a step of administering a pharmaceutically effective amount of the fusion protein provided in the present disclosure, and a suitable total daily dose of the fusion protein may be determined by an attending physician within the scope of sound medical judgment. The fusion protein may be administered once or several times a day. However, for the purpose of the present disclosure, a specific therapeutic dose for a particular patient is preferably determined depending on various factors, including the kind and degree of response to be achieved, whether other formulation is used in some cases, the patient’s age, body weight, general health condition, sex and diet, the duration of administration, the route of administration, the excretion rate of the composition comprising the active ingredient, the period of treatment, and drugs that are used together with or simultaneously with the specific composition, as well as similar factors well known in the medical field.

Meanwhile, the method for preventing or treating inflammatory disease and immune-related disease may be a combination therapy further comprising administering a compound or substance having therapeutic activity against one or more diseases, but is not limited thereto.

In the present disclosure, the “combination” is to be understood to refer to simultaneous, separate or sequential administration. Where the administration is sequential or separate, the delay in administering the second component should not be such as to lose the benefit of the effect arising from use of the combination.

In the present disclosure, the fusion protein, the inflammatory disease and the immune-related disease are as defined above, and thus will be omitted in the following description in order to avoid excessive complexity of the specification.

According to yet further another embodiment of the present disclosure, there is provided a method for preventing or treating cancer comprising a step of administering to a subject a pharmaceutically effective amount of any one or more of: the fusion protein according to the present disclosure; the expression vector; and the host cell.

In the present disclosure, the fusion protein, the cancer, the subject and the like are as defined above, and thus will be omitted in the following description in order to avoid excessive complexity of the specification.

[Sequence List]

```
SEQ ID NO. 1: Full-length amino acid sequence of BAF57
MSKRPSYAPP PTPAPATQMP STPGFVGYNP YSHLAYNNYR LGGNPGTNSR VTASSGITIP   60
MPPKPPDKPL MPYMRYSRKV WDQVKASNPD LKLWEIGKII GGMWRDLTDE EKQEYLNEYE  120
AEKIEYNESM KAYHNSPAYL AYINAKSRAE AALEEESRQR QSRMEKGEPY NSIQPAEDPD  180
DYDDGFSMKH TATARFQRNH RLISEILSES VVPDVRSVVT TARMQVLKRQ VQSLMVHQRK  240
LEAELLQIEE RHQEKKRKFL ESTDSFNNEL KRLCGLKVEV DMEKIAAEIA QAEEQARKRQ  300
EEREKEAAEQ AERSQSSIVP EEEQAANKGE EKKDDENIPM ETEETHLEET TESQQNGEEG  360
TSTPEDKESG QEGVDSMAEE GTSDSNTGSE SNSATVEEPP TDPIPEDEKK E

SEQ ID NO. 2: Full-length nucleotide sequence of BAF57
atgtcaaaaa gaccatctta tgccccacct cccaccccag ctcctgcaac acaaatgccc   60
agcacaccag ggtttgtggg atacaatcca tacagtcatc tcgcctacaa caactacagg  120
ctgggaggga acccgggcac caacagccgg gtcacggcat cctctggtat cacgattcca  180
aaacccccaa agccaccaga taagccgctg atgccctaca tgaggtacag cagaaaggtc  240
tgggaccaag taaaggcttc caaccctgac ctaaagttgt gggagattgg caagattatt  300
ggtggcatgt ggcgagatct cactgatgaa gaaaaacaag aatatttaaa cgaatacgaa  360
gcagaaaaga tagagtacaa tgaatctatg aaggcctatc ataattcccc cgcgtacctt  420
gcttacataa atgcaaaaag tcgtgcagaa gctgctttag aggaagaaag tcgacagaga  480
caatctcgca tggagaaagg agaaccgtac atgagcattc agcctgctga agatccagat  540
gattatgatg atggcttttc aatgaagcat acagccaccg cccgtttcca gagaaaccac  600
cgcctcatca gtgaaattct tagtgagagt gtggtgccag acgttcggtc agttgtcaca  660
acagctagaa tgcaggtcct caaacggcag gtccagtcct taatggttca tcagcgaaaa  720
ctagaagctg aacttcttca aatagaggaa cgacaccagg agaagaagag gaaattcctg  780
gaaagcacag attcatttaa caatgaactt aaaaggttgt gcggtctgaa agtagaagtg  840
gatatggaga aaattgcagc tgagattgca caggcagagg aacaggcccg caaaaggcag  900
gaggaaaggg agaaggaggc cgcagagcaa gctgagcgca gtcagagcag catcgttcct  960
gaggaagaac aagcagctaa caaaggcgag gagaagaaag acgacgagaa cattccgatg 1020
gagacagagg agacacacct tgaagaaaca acagagagcc aacagaatgg tgaagaaggc 1080
acgtctactc ctgaggacaa ggagagtggg caggaggggg tcgacagtat ggcagaggaa 1140
ggaaccagtg atagtaacac tggctcggag agcaacagtg caacagtgga ggagccacca 1200
acagatccca taccagaaga tgagaaaaaa gaa

SEQ ID NO. 3: Amino acid sequence of BAF57 fragment
AYHNSPAYLA YINAKSRAEA ALEEESRQRQ SRMEKGEPYM SIQPAEDPDD YDDGFSMKHT   60
ATARFQRNHR LISEILSESV VPDVRSVVTT ARMQVLKRQV QSLMVHQRKL EAELLQIEER  120
```

-continued

[Sequence List]

HQEKKRKFLE STDSFNNELK RLCGLKVEVD MEKIAAEIAQ AEEQARKRQE EREKEAAEQA 180
ERSQSSIVPE EEQAANKGEE KKDDENIPME TEETHLEETT ESQQNGEEGT STPEDKESGQ 240
EGVDSMAEEG TSDSNTGSES NSATVEEPPT DPIPEDEKKE

SEQ ID NO. 4: Nucleotide sequence of BAF57 fragment
GCCTATCATA ATTCCCCCGC GTACCTTGCT TACATAAATG CAAAAAGTCG TGCAGAAGCT 60
GCTTTAGAGG AAGAAAGTCG ACAGAGACAA TCTCGCATGG AGAAAGGAGA ACCGTACATG 120
AGCATTCAGC CTGCTGAAGA TCCAGATGAT TATGATGATG GCTTTTCAAT GAAGCATACA 180
GCCACCGCCC GTTTCCAGAG AAACCACCGC CTCATCAGTG AAATTCTTAG TGAGAGTGTG 240
GTGCCAGACG TTCGGTCAGT TGTCACAACA GCTAGAATGC AGGTCCTCAA ACGGCAGGTC 300
CAGTCCTTAA TGGTTCATCA GCGAAAACTA GAAGCTGAAC TTCTTCAAAT AGAGGAACGA 360
CACCAGGAGA AGAAGAGGAA ATTCCTGGAA AGCACAGATT CATTTAACAA TGAACTTAAA 420
AGGTTGTGCG GTCTGAAAGT AGAAGTGGAT ATGGAGAAAA TTGCAGCTGA GATTGCACAG 480
GCAGAGGAAC AGGCCCGCAA AAGGCAGGAG GAAAGGGAGA AGGAGGCCGC AGAGCAAGCT 540
GAGCGCAGTC AGAGCAGCAT CGTTCCTGAG GAAGAACAAG CAGCTAACAA AGGCGAGGAG 600
AAGAAAGACG ACGAGAACAT TCCGATGGAG ACAGAGGAGA CACACCTTGA AGAAACAACA 660
GAGAGCCAAC AGAATGGTGA AGAAGGCACG TCTACTCCTG AGGACAAGGA GAGTGGGCAG 720
GAGGGGGTCG ACAGTATGGC AGAGGAAGGA ACCAGTGATA GTAACACTGG CTCGGAGAGC 780
AACAGTGCAA CAGTGGAGGA GCCACCAACA GATCCCATAC CAGAAGATGA GAAAAAAGAA

[SEQ ID NO. 5: Amino acid sequence of Hph-1
YARVRRRGPR R

SEQ ID NO. 6: Nucleotide sequence of Hph-1
tatgcacgtg ttcggaggcg tggaccccgc cgc

SEQ ID NO. 7: Amino acid sequence of FLAG tag
DYKDDDDK

SEQ ID NO. 8: Nucleotide sequence of FLAG tag
gactacaagg acgacgatga caag

SEQ ID NO. 9: Amino acid sequence of a recombinant fusion protein according to one embodiment of the present disclosure
YARVRRRGPR RAYHNSPAYL AYINAKSRAE AALEEESRQR QSRMEKGEPY NSIQPAEDPD 60
DYDDGFSMKH TATARFQRNH RLISEILSES VVPDVRSVVT TARMQVLKRQ VQSLMVHQRK 120
LEAELLQIEE RHQEKKRKFL ESTDSFNNEL KRLCGLKVEV DMEKIAAEIA QAEEQARKRQ 180
EEREKEAAEQ AERSQSSIVP EEEQAANKGE EKKDDENIPM ETEETHLEET TESQQNGEEG 240
TSTPEDKESG QEGVDMSAEE GTSDSNTGSE SNSATVEEPP TDPIPEDEKK E SEQ ID NO. 10: Amino acid sequence of a recombinant fusion protein according to one embodiment of the present disclosure
YARVRRRGPR RDYKDDDDKA YHNSPAYLAY INAKSRAEAA LEEESRQRQS RMEKGEPYMS 60
YQPAEDPDDY DDGFSMKHTA TARFQRNHRL ISEILSESVV PDVRSVVTTA RMQVLKRQVQ 120
SLMVHQRKLE AELLQIEERH QEKKRKFLES TDSFNNELKR LCGLKVEVDM EKIAAEIAQA 180
EEQARKRQEE REKEAAEQAE RSQSSIVPEE EQAANKGEEK KDDENIPMET EETHLEETTE 240
SQQNGEEGTS TPEDKESGQE GVDSMAEEGT SDSNTGSESN SATVEEPPTD PIPEDEKKE SEQ ID NO. 11: Amino acid sequence (ntBAF57-ΔPH) of a recombinant fusion protein according to one embodiment of the present disclosure
MGSSHHHHHH SSGLVPRGSH MASGYARVRR RGPRRGDYKD DDDKEFGAYH NSPAYLAYIN 60
AKSRAEAALE EESRQRQSRM EKGEPYMSIQ PAEDPDDYDD GFSMKHTATA RFQRNHRLIS 120
EILSESVVPD VRSVVTTARM QVLKRQVQSL MVHQRKLEAE LLQIEERHQE KKRKFLESTD 180
SNFFELKRLC GLKVEVDMEK IAAEIAQAEE QARKRQEERE KEAAEQAERS QSSIVPEEEQ 240
AANKGEEKKD DENIPMETEE THLEETTESQ QNGEEGTSTP EDKESGQEGV DSMAEEGTSD 300
SNTGSESNSA TVEEPPTDPI PEDEKKE SEQ ID NO. 12: Nucleotide sequence of a recombinant fusion protein according to one embodiemtn of the present disclusure
tatgcacgtg ttcggaggcg tggaccccgc cgcgcctatc ataattcccc cgcgtacctt 60
gcttacataa atgcaaaaag tcgtgcagaa gctgctttag aggaagaaag tcgacagaga 120
caatctcgca tggagaaagg agaaccgtac atgagcattc agcctgctga agatccagat 180
gattatgatg atggcttttc aatgaagcat acagccaccg cccgtttcca gagaaaccac 240
cgcctcatca gtgaaattct tagtgagagt gtggtgccag acgttcggtc agttgtcaca 300
acagctagaa tgcaggtcct caaacggcag gtccagtcct taatggttca tcagcgaaaa 360
ctagaagctg aacttcttca aatagaggaa cgacaccagg agaagaagag gaaattcctg 420
gaaagcacag attcatttaa caatgaactt aaaaggttgt gcggtctgaa agtagaagtg 480
gatatggaga aaattgcagc tgagattgca caggcagagg aacaggcccg caaaaggcag 540
gaggaaaggg agaaggaggc cgcagagcaa gctgagcgca gtcagagcag catcgttcct 600
gaggaagaac aagcagctaa caaaggcgag gagaagaaag acgacgagaa cattccgatg 660
gagacagagg agacacacct tgaagaaaca acagagagcc aacagaatgg tgaagaaggc 720
acgtctactc ctgaggacaa ggagagtggg caggaggggg tcgacagtat ggcagaggaa 780
ggaaccagtg atagtaacac tggctcggag agcaacagtg caacagtgga ggagccacca 840
acagatccca taccagaaga tgagaaaaaa gaa SEQ ID NO. 13: Nucleotide sequence of a recombinant fusion protein according to one embodiment of the present disclosure -continued

[Sequence List]

```
tatgcacgtg ttcggaggcg tggaccccgc cgcgactaca aggacgacga tgacaaggcc   60
tatcataatt cccccgcgta ccttgcttac ataaatgcaa aaagtcgtgc agaagctgct  120
ttagaggaag aaagtcgaca gagacaatct cgcatggaga aaggagaacc gtacatgagc  180
attcagcctg ctgaagatcc agatgattat gatgatggct tttcaatgaa gcatacagcc  240
accgcccgtt tccagagaaa ccaccgcctc atcagtgaaa ttcttagtga gagtgtggtg  300
ccagacgttc ggtcagttgt cacaacagct agaatgcagg tcctcaaacg gcaggtccag  360
tccttaatgg ttcatcagcg aaaactagaa gctgaacttc ttcaaataga ggaacgacac  420
caggagaaga agaggaaatt cctggaaagc acagattcat ttaacaatga acttaaaagg  480
ttgtgcggtc tgaaagtaga agtggatatg gagaaaattg cagctgagat tgcacaggca  540
gaggaacagg cccgcaaaag gcaggaggaa agggagaagg aggccgcaga gcaagctgag  600
cgcagtcaga gcagcatcgt tcctgaggaa gaacaagcag ctaacaaagg cgaggagaag  660
aaagacgacg agaacattcc gatggagaca gaggagacac accttgaaga aacaacagag  720
agccaacaga atggtgaaga aggcacgtct actcctgagg acaaggagag tgggcaggag  780
ggggtcgaca gtatggcaga ggaaggaacc agtgatagta acactggctc ggagagcaac  840
agtgcaacag tggaggagcc accaacagat cccataccag aagatgagaa aaaagaa
```

SEQ ID NO. 14: Nucleotide sequence (ntBAF57-ΔPH) of a recombinant fusion protein according to one embodiment of the present disclosure

```
atgggcagca gccatcatca tcatcatcac agcagcggcc tggtgccgcg cggcagccat   60
atggctagcg gctatgcacg tgttcggagg cgtggacccc gccgcggcga ctacaaggac  120
gacgatgaca aggaattcgg agcctatcat aattcccccg cgtaccttgc ttacataaat  180
gcaaaaagtc gtgcagaagc tgctttagag gaagaaagtc gacagagaca atctcgcatg  240
gagaaaggag aaccgtacat gagcattcag cctgctgaag atccagatga ttatgatgat  300
ggcttttcaa tgaagcatac agccaccgcc cgtttccaga gaaaccaccg cctcatcagt  360
gaaattctta gtgagagtgt ggtgccagac gttcggtcag ttgtcacaac agctagaatg  420
caggtcctca aacggcaggt ccagtcctta atggttcatc agcgaaaact agaagctgaa  480
cttcttcaaa tagaggaacg acaccaggag aagaagagga aattcctgga aagcacagat  540
tcatttaaca atgaacttaa aaggttgtgc ggtctgaaag tagaagtgga tatggagaaa  600
attgcagctg agattgcaca ggcagaggaa caggcccgca aaaggcagga ggaaagggag  660
aaggaggccg cagagcaagc tgagcgcagt cagagcagca tcgttcctga ggaagaacaa  720
gcagctaaca aaggcgagga gaagaaagac gacgagaaca ttccgatgga gacagaggag  780
acacaccttg aagaaacaac agagagccaa cagaatggtg aagaaggcac gtctactcct  840
gaggacaagg agagtgggca ggagggggtc gacagtatgg cagaggaagg aaccagtgat  900
agtaacactg gctcggagag caacagtgca acagtggagg agccaccaac agatcccata  960
ccagaagatg agaaaaaaga atag
```

SEQ ID NO. 15: Amino acid sequence (BAF57-ΔPH) of a recombinant fusion protein as a comparative example

```
MGSSHHHHHH SSGLVPRGSH MASDYKDDDD KEFGAYHNSP AYLAYINAKS RAEAALEEES   60
RQRQSRMEKG EPYMSIQPAE DPDDYDDGFS MKHTATARFQ RNHRLISEIL SESVVPDVRS  120
VVTTARMQVL KRQVQSLMVH QRKLEAELLQ IEERHQEKKR EFLESTDSFN NELKRLCGLK  180
VEVDMEKIAA EIAQAEEQAR KRQEEREKEA AEQAERSQSS IVPEEEQAAN KGEEKKDDEN  240
IPMETEETHL EETTESQQNG EEGTSTPEDK ESGQEGVDSM AEEGTSDSNT GSESNSATVE  300
EPPTDPIPED EKKE
```

SEQ ID NO. 16: Nucleotide sequence (BAF57-ΔPH) of a recombinant fusion protein as a comparative example

```
atgggcagca gccatcatca tcatcatcac agcagcggcc tggtgccgcg cggcagccat   60
atggctagcg actacaagga cgacgatgac aaggaattcg gagcctatca taattccccc  120
gcgtaccttg cttacataaa tgcaaaaagt cgtgcagaag ctgctttaga ggaagaaagt  180
cgacagagac aatctcgcat ggagaaagga gaaccgtaca tgagcattca gcctgctgaa  240
gatccagatg attatgatga tggcttttca atgaagcata cagccaccgc ccgtttccag  300
agaaaccacc gcctcatcag tgaaattctt agtgagagtg tggtgccaga cgttcggtca  360
gttgtcacaa cagctagaat gcaggtcctc aaacggcagg tccagtcctt aatggttcat  420
cagcgaaaac tagaagctga acttcttcaa atagaggaac gacaccagga gaagaagagg  480
gaattcctgg aaagcacgga ttcatttaac aatgaactta aaaggttgtg cggtctgaaa  540
gtagaagtgg atatggagaa aattgcagct gagattgcac aggcagagga acaggcccgc  600
aaaaggcagg aggaaaggga gaaggaggcc gcagagcaag ctgagcgcag tcagagcagc  660
atcgttcctg aggaagaaca agcagctaac aaaggcgagg agaagaaaga cgacgagaac  720
attccgatgg agacagagga gacacacctt gaagaaacaa cagagagcca acagaatggt  780
gaagaaggca cgtctactcc tgaggacaag gagagtgggc aggagggggt cgacagtatg  840
gcagaggaag gaaccagtga tagtaacact ggctcggaga gcaacagtgc aacagtggag  900
gagccaccaa cagatcccat accagaagat gagaaaaaag aatag
```

BRIEF DESCRIPTION OF THE DRAWINGS

FIG. 1 schematically shows a BAF57 wild-type protein, a ntBAF57-ΔPH recombinant fusion protein according to one embodiment of the present disclosure, and a BAF57-ΔPH recombinant fusion protein as a control, constructed in Example 1.

FIG. 2 shows the results of performing Western blot analysis of the ntBAF57-ΔPH recombinant fusion protein according to one embodiment of the present disclosure in Example 1.

FIG. 3 shows the results obtained by treating with CD4+ T cells with various concentrations of the ntBAF57-ΔPH recombinant fusion protein according to one embodiment of the present disclosure in Example 2, and then analyzing the expression level of the recombinant fusion protein in the cells.

FIG. 4 shows the results obtained by treating with CD4+ T cells with the ntBAF57-ΔPH recombinant fusion protein according to one embodiment of the present disclosure for different periods of time in Example 2, and then analyzing the expression level of the recombinant fusion protein in the cells.

FIG. 5 shows photographs obtained by treating HeLa cells with the ntBAF57-ΔPH recombinant fusion protein according to one embodiment of the present disclosure in Example 2, and then photographing the position of the recombinant fusion protein delivered into the cells by the use of a confocal microscope.

FIG. 6 shows the results obtained by treating mouse CD4+ T cells with various concentrations of the ntBAF57-ΔPH recombinant fusion protein according to one embodiment of the present disclosure in Example 3, and then analyzing the viability of the cells.

FIG. 7 shows the results obtained by treating Jurkat T cells with various concentrations of the ntBAF57-ΔPH recombinant fusion protein according to one embodiment of the present disclosure in Example 3, and then analyzing the viability of the cells.

FIG. 8 shows the results obtained by activating naïve CD4+ T cells in Example 4, treating the activated cells with various concentrations of the ntBAF57-ΔPH recombinant fusion protein according to one embodiment of the present disclosure, and then analyzing the expression level of CD69, a marker of early T-cell activation, in the treated cells.

FIG. 9 shows the results obtained by activating naïve CD4+ T cells in Example 4, treating the activated cells with various concentrations of the ntBAF57-ΔPH recombinant fusion protein according to one embodiment of the present disclosure, and then analyzing the expression level of CD25, an activation marker of T cells, in the treated cells.

FIG. 10 shows the results obtained by activating naïve CD4+ T cells in Example 4, treating the activated cells with various concentrations of the ntBAF57-ΔPH recombinant fusion protein according to one embodiment of the present disclosure, and then analyzing the amount of interleukin-2 secreted in a culture of the cells, in the treated cells.

FIG. 11 shows the results obtained by activating naïve CD4+ T cells in Example 4, treating the activated cells with various concentrations of the ntBAF57-ΔPH recombinant fusion protein according to one embodiment of the present disclosure, and then analyzing the expression level of CD69 in the cells.

FIG. 12 shows the results obtained by activating naïve CD4+ T cells in Example 4, treating the activated cells with the ntBAF57-ΔPH recombinant fusion protein according to one embodiment of the present disclosure for different periods of time, and then analyzing the expression level of CD69 in the cells.

FIG. 13 shows the results obtained by treating naïve CD4+ T cells with the ntBAF57-ΔPH recombinant fusion protein according to one embodiment of the present disclosure in Example 5, activating the cells, and then analyzing the expression level of phosphorylated protein in the cells.

FIG. 14 shows the results obtained by treating naïve CD4+ T cells with the ntBAF57-ΔPH recombinant fusion protein according to one embodiment of the present disclosure in Example 5, activating the treated cells, and then analyzing the expression levels of phosphorylated ZAP70 and Erk in the cells.

FIG. 15 shows the results obtained by treating Jurkat T cells with the ntBAF57-ΔPH recombinant fusion protein according to one embodiment of the present disclosure in Example 5, activating the cells, and then analyzing the expression levels of Erk and Akt and expression levels of phosphorylated Erk and Akt in the cells.

FIG. 16 shows the results obtained by activating naïve CD4+ T cells in Example 6, treating the cells with the ntBAF57-ΔPH recombinant fusion protein according to one embodiment of the present disclosure, and then analyzing the expression level of NFAT1 in the cells.

FIG. 17 shows the results obtained by activating naïve CD4+ T cells in Example 6, treating the cells with the ntBAF57-ΔPH recombinant fusion protein according to one embodiment of the present disclosure, and then analyzing the expression level of p65 in the cells.

FIG. 18 shows the results obtained by activating naïve CD4+ T cells in Example 6, treating the cells with the ntBAF57-ΔPH recombinant fusion protein according to one embodiment of the present disclosure, and then analyzing the expression level of c-Fos in the cells.

FIG. 19 shows the results obtained by activating naïve CD4+ T cells in Example 6, treating the cells with the ntBAF57-ΔPH recombinant fusion protein according to one embodiment of the present disclosure, and then analyzing the expression level of phospho c-Fos in the cells.

FIG. 20 shows the results obtained by activating naïve CD4+ T cells in Example 7, treating the cells with the ntBAF57-ΔPH recombinant fusion protein according to one embodiment of the present disclosure, and then analyzing whether the recombinant fusion protein would be present in a precipitated BAF155 complex.

FIG. 21 shows the results obtained by activating naïve CD4+ T cells in Example 7, treating the cells with the ntBAF57-ΔPH recombinant fusion protein according to one embodiment of the present disclosure, and then analyzing the expression level of BAF57 in the CD4+ T cells.

FIG. 22 shows the results obtained by activating naïve CD4+ T cells in Example 7, treating the cells with the ntBAF57-ΔPH recombinant fusion protein according to one embodiment of the present disclosure, and then analyzing the expression level of BAF57 in the CD4+ T cells.

FIG. 23 shows the results obtained by activating naïve CD4+ T cells in Example 8, treating the cells with the ntBAF57-ΔPH recombinant fusion protein according to one embodiment of the present disclosure, and then analyzing the mRNA expression levels of BAF57 and BAF155 in the cells.

FIG. 24 shows the results obtained by activating naïve CD4+ T cells in Example 9, treating the activated cells with the proteasome inhibitor MG132 or the lysosomal inhibitor $NH_4Cl$ together with the ntBAF57-ΔPH recombinant fusion protein according to one embodiment of the present disclosure, and then analyzing the expression level of CD69 in the cells.

FIG. 25 shows the results obtained by activating naïve CD4+ T cells in Example 9, treating the activated cells with the proteasome inhibitor MG132 or the lysosomal inhibitor $NH_4Cl$ together with the ntBAF57-ΔPH recombinant fusion protein according to one embodiment of the present disclosure, and then analyzing the expression level of BAF155 in the cells.

FIG. 26 shows an experimental protocol for carrying out an experiment of the ntBAF57-ΔPH recombinant fusion protein according to one embodiment of the present disclosure on an LPS-induced sepsis mouse model in Example 10.

FIG. 27 shows the results obtained by treating the LPS-induced sepsis mouse model with the ntBAF57-ΔPH recombinant fusion protein according to one embodiment of the present disclosure in Example 10, and then analyzing the survival rate of the mice.

FIG. 28 shows the results obtained by treating the LPS-induced sepsis mouse model with the ntBAF57-ΔPH recombinant fusion protein according to one embodiment of the present disclosure in Example 10, and then analyzing the expression level of TNF-α in the mouse serum.

FIG. 29 shows the results obtained by treating the LPS-induced sepsis mouse model with the ntBAF57-ΔPH recombinant fusion protein according to one embodiment of the present disclosure in Example 10, and then analyzing the expression level of IL-1β in the mouse serum.

FIG. 30 shows the results obtained by treating the LPS-induced sepsis mouse model with the ntBAF57-ΔPH recombinant fusion protein according to one embodiment of the present disclosure in Example 10, and then analyzing the proportion of CD4+CD69+ T cells in the mouse spleen.

FIG. 31 shows the results obtained by treating the LPS-induced sepsis mouse model with the ntBAF57-ΔPH recombinant fusion protein according to one embodiment of the present disclosure in Example 10, and then analyzing the expression level of BAF57 protein in the CD4+CD69+ T cells, in the mouse spleen.

DESCRIPTION OF SPECIFIC EMBODIMENTS

Hereinafter, the present disclosure will be described in more detail with reference to examples. However, these examples are only to explain the present disclosure in more detail, and it will be obvious to those skilled in the art that the scope of the present disclosure according to the gist of the present disclosure is not limited by these examples.

EXAMPLES

[Example 1] Construction of Recombinant Fusion Proteins for Inhibiting Function of BAF57

As shown in FIG. 1, recombinant DNAs were constructed. Specifically, to the N-terminus of a BAF57-PH domain (SEQ ID NO: 4) obtained by removing an HMG domain, which is a DNA binding domain, and a proline-rich domain, which is an N-terminal portion, from BAF57, the protein transduction domain Hph-1 (SEQ ID NO: 6) and a FLAG tag (SEQ ID NO: 8) were fused, thereby constructing a recombinant DNA (ntBAF57-ΔPH; SEQ ID NO: 14). In addition, as a control, a recombinant DNA (BAF57-ΔPH; SEQ ID NO: 16) was constructed by fusing only a FLAG tag (SEQ ID NO: 8) to the N-terminus of a BAF57-PH domain (SEQ ID NO: 4). Each of these recombinant DNAs was cloned into a pET28a(+) plasmid, and then transformed into a BL21 Codon Plus (DE3)-RIPL strain. Each of the transformed strains was cultured at 37° C., and then 1 mM IPTG (isopropyl-β-D-thiogalactopyranoside, Duchefa) was added thereto, followed by culture at 37° C. for 6 hours. After 6 hours, the cultured cells were collected, lysed with lysis buffer (10 mM imidazole, 300 mM NaCl, 50 mM $NaH_2PO_4$, pH 8.0), and then disrupted using a homogenizer at 4° C. for 10 minutes. The supernatant was separated from the disrupted cell solution, mixed with Ni-NTA beads, and then incubated at 4° C. for 1 hour. Next, the bead-bound solution was added to a column (Poly-prep Chromatography Columns, BIO-RAD), and non-specifically bound protein was sufficiently washed out with washing buffer (30 mM imidazole, 300 mM NaCl, 50 mM $NaH_2PO_4$, pH 8.0), and then each recombinant protein was separated from the beads using elution buffer (250 mM imidazole, 300 mM NaCl, 50 mM $NaH_2PO_4$, pH 8.0). For application to a cell experiment, to change the buffer composition to PBS, each of the purified proteins was added to a PD-10 column (GE Healthcare) and purified with 10% glycerol PBS buffer. Next, the protein was stored at −80° C. To confirm the size and concentration of the purified protein (ntBAF57-ΔPH: SEQ ID NO: 11; BAF57-ΔPH: SEQ ID NO: 15), each protein was analyzed by Coomassie blue staining following SDS-PAGE, and the size and purity of each protein were analyzed by Western blotting using a FLAG tag. The results are shown in FIG. 2.

[Example 2] Examination of Intracellular Delivery Ability of Recombinant Fusion Proteins 1. Analysis of Intracellular Delivery Ability of Recombinant Fusion Proteins at Various Treatment Concentrations In order to confirm whether the recombinant fusion proteins constructed by the method of Example 1 above would be delivered into the cytoplasm and nucleus of cells through the cell membrane, $10^6$ mouse CD4+ T cells were treated with various concentrations (0.5 μM to 4 μM) of the ntBAF57-ΔPH recombinant fusion protein for 1 hour. As a negative control group, $10^6$ mouse CD4+ T cells were treated with 4 μM of the BAF57-ΔPH recombinant fusion protein. Next, to examine the amount of each of the proteins present in the cells, the cells were fixed with fixation/permeabilization buffer (eBioscience), and then stained with anti-FLAG-FITC antibody (Sigma Aldrich). In addition, the amount of the stained cells was measured using FACS Calibur (BD Bioscience) and analyzed using the Flowjo V10 program.

As a result, as shown in FIG. 3, it was confirmed that as the CD4+ T cells were treated with a higher concentration of the ntBAF57-ΔPH recombinant fusion protein, the expression level of the protein in the cells increased. However, in the case of the BAF57-ΔPH recombinant fusion protein that does not comprise the protein transduction domain, it could be confirmed that the protein did not enter the cells.

2. Analysis of Intracellular Delivery Ability of Recombinant Fusion Protein for Different Treatment Periods of Time $10^6$ mouse CD4+ T cells were treated with the ntBAF57-ΔPH recombinant fusion protein for different periods of time (1 to 24 hours), and the expression level of the protein in the cells was analyzed in the same manner as described in the above section 1. The results are shown in FIG. 4.

As a result, as shown in FIG. 4, it could be confirmed that from when the CD4+ T cells were treated with the ntBAF57-ΔPH recombinant fusion protein for 1 hour, the protein was found in the cells, and the protein was present in the cells up to 24 hours.

3. Analysis of Intracellular Position of Recombinant Fusion Protein

Next, in order to analyze the intracellular position of the ntBAF57-ΔPH recombinant fusion protein, $5\times10^4$ HeLa cells were treated with the ntBAF57-ΔPH recombinant fusion protein for 1 hour, and then the remaining protein was washed out with PBS. Thereafter, the cells were fixed with 4% formaldehyde and 0.2% Triton X-100 (Sigma Aldrich), and then the protein was stained with anti-FLAG-FITC antibody. Next, the nucleus of the cells was stained with DAPI, and then the position of the recombinant fusion protein delivered into the cells was observed using a confocal microscope (Carl Zeiss). The results are shown in FIG. 5.

As shown in FIG. 5, most of the ntBAF57-ΔPH recombinant fusion protein delivered into the cells moved to and was positioned in the nucleus of the cells, and the protein was also observed in some cytoplasm.

[Example 3] Evaluation of Cytotoxicity of Recombinant Fusion Protein

In order to examine whether the ntBAF57-ΔPH recombinant fusion protein constructed by the method of Example 1 would show side effects due to cytotoxicity after intracellular delivery, a cytotoxicity experiment was performed. Specifically, $1\times10^5$ mouse CD4+ T cells or Jurkat T cells were treated with various concentrations (0.1 μM to 4 μM) of the ntBAF57-ΔPH recombinant fusion protein for 24 hours, and then treated with CCK-8 and cultured at 37° C. for 4 hours. Next, the viability of the cells was measured, and the results of the measurement are shown in FIGS. 6 and 7.

As shown in FIGS. 6 and 7, it could be confirmed that even when the mouse CD4+ T cells or Jurkat T cells were treated with up to 4 μM of the ntBAF57-ΔPH recombinant fusion protein, the protein did not affect the growth of the cells.

[Example 4] Analysis of the Function of ntBAF57-ΔPH Recombinant Fusion Protein in T-Cell Activation Process 1. Analysis of Expression of CD69, a Marker of Early T-Cell Activation To analyze the function of BAF57 in a T-cell activation process using the ntBAF57-ΔPH recombinant fusion protein, mouse naïve CD4+ T cells were extracted from the splenocytes of normal C57BL/6 mice and activated by anti-CD3/CD28 antibody (BD Pharmingen; 2 μg/ml). Simultaneously with the activation, the cells were treated with various concentrations (1 μM to 4 μM) of the ntBAF57-ΔPH recombinant fusion protein, and after 12 hours, the expression level of CD69, which is a marker of early T-cell activation, in the treated cells, was analyzed by flow cytometry. The results of the analysis are shown in FIG. 8.

As shown in FIG. 8, it was confirmed that the expression level of CD69 in the cells treated with the ntBAF57-ΔPH recombinant fusion protein significantly decreased in a concentration-dependent manner, and activation of the cells was inhibited to an extent similar to that of cells treated with cyclosporin A which is used as an immunosuppressive drug.

2. Analysis of T-Cell Activation Marker CD25

In addition, in order to analyze the expression level of another T-cell activation marker CD25, naïve CD4+ T cells were activated with anti-CD3/CD28 antibody and, at the same time, treated with various concentrations (1 μM to 4 μM) of the ntBAF57-ΔPH recombinant fusion protein. 48 Hours after the treatment, the expression level of CD25 in the cells was analyzed by flow cytometry, and the results of the analysis are shown in FIG. 9.

As shown in FIG. 9, it was confirmed that, like the expression level of CD69 in the cells treated with the ntBAF57-ΔPH recombinant fusion protein, the expression level of CD25 decreased in a manner dependent on the concentration of the recombinant fusion protein, and the effect of inhibiting the expression of CD25 was higher than that in the group treated with cyclosporin A.

3. Evaluation of Inhibitory Effect on Interleukin-2 Secretion of Caused by T-Cell Activation In addition, in order to examine whether the secretion of interleukin-2 (IL-2) by T-cell activation would be inhibited by the ntBAF57-ΔPH recombinant fusion protein, mouse naïve CD4+ T cells were provided with an activation signal by anti-CD3/CD28 antibody and, at the same time, treated with various concentrations (1 μM to 4 μM) of the ntBAF57-ΔPH recombinant fusion protein, followed by culture for 48 hours. In addition, the cell culture was collected. The expression level of interleukin-2 in the cell culture was measured by interleukin-2 ELISA kit (eBioscience), and the results are shown in FIG. 10.

As shown in FIG. 10, it could be confirmed that the secretion of interleukin-2 from the cells treated with the ntBAF57-ΔPH recombinant fusion protein significantly decreased.

4. Analysis of T-Cell Activation Inhibitory Mechanism

In order to analyze the mechanism by which a T-cell activation signal would be inhibited by the ntBAF57-ΔPH recombinant fusion protein, whether T-cell activation would be inhibited was examined by treatment with the recombinant fusion protein for different period of time. Specifically, mouse naïve CD4+ T cells were isolated, and then activated by anti-CD3/CD28 antibody for 24 hours. After 24 hours, the cells were treated with various concentrations (1 μM to 4 μM) of the ntBAF57-ΔPH recombinant fusion protein, and the expression level of CD69 in the cell was analyzed by flow cytometry.

As shown in FIG. 11, it could be confirmed that when the T cells were treated with the ntBAF57-ΔPH recombinant fusion protein simultaneously with T-cell activation, the expression of CD69 in the cells was inhibited, but when the cells were treated with the recombinant fusion protein after 24 hours, the expression of CD69 in the cells was not inhibited.

In addition, with reference to a previous document indicating that a T-cell activation signal is transduced within a short time, the mouse naïve CD4+ T cells were treated with 4 μM of the ntBAF57-ΔPH recombinant fusion protein at 10 minutes, 30 minutes, 1 hour, 3 hours, 6 hours, 12 hours and 24 hours after activation of the cells, and the expression level of CD69 in the cells was analyzed by flow cytometry.

As shown in FIG. 12, it could be confirmed that as the T cells were treated with the ntBAF57-ΔPH recombinant fusion protein earlier after T-cell activation signaling, the effect of inhibiting the expression of CD69 was better.

Through the above results, it could be predicted that the effect of the ntBAF57-ΔPH recombinant fusion protein on the inhibition of T-cell activation would inhibit T-cell receptor proximal signaling, which occur in early activation signaling events, or inhibit the expression of the gene.

[Example 5] Evaluation of the Inhibitory Effect of ntBAF57-ΔPH Recombinant Fusion Protein on Phosphorylation of T-Cell Activation Signaling Protein In order to examine the mechanism by which the ntBAF57-ΔPH recombinant fusion protein exhibits an inhibitory effect on T-cell activation, phosphorylation of signaling-mediated protein playing the most important role in the early signaling system was analyzed. When T cells are stimulated by CD3 and CD28, signaling protein transduces a signal into the cells by phosphorylation within 10 minutes, and hence major transcription factors such as NFAT, NF-kB and AP-1 are expressed. Thus, since the above experiment showed that the ntBAF57-ΔPH recombinant fusion protein exhibited an inhibitory effect on early T-cell activation, whether the recombinant fusion protein would affect tyrosine phosphorylation caused by the activating signal was analyzed. For this, $2\times10^6$ mouse naïve CD4+ T cells were isolated and treated with the ntBAF57-ΔPH recombinant fusion protein (1 μM or 4 μM) at 37° C. for 1 hour, and then anti-CD3/CD28 antibody (5 μg/ml) was allowed to bind to the cell surface at 4° C. for 30 minutes, followed by activation of the cells at 37° C. for 10 minutes. After 10 minutes, the cells were lysed with RIPA buffer, and then subjected to Western blotting using anti-phospho tyrosine antibody (1:1,000; Cell Signaling).

As shown in FIG. 13, it could be confirmed that the amount of phosphorylated protein in the activated T cells significantly increased compared to that in the naïve CD4+ T cells. Also, it could be confirmed that treatment with the ntBAF57-ΔPH recombinant fusion protein or cyclosporin A inhibited T-cell activation by reducing the amount of phosphorylated protein.

In addition, the phosphorylation levels of ZAP70 and Erk known as the most important signaling proteins in the T-cell activation process were compared. Specifically, $2\times10^6$ mouse naïve CD4+ T cells were isolated and treated with the ntBAF57-ΔPH recombinant fusion protein (1 μM or 4 μM) at 37° C. for 1 hour, and then anti-CD3/CD28 antibody (5 μg/ml) was allowed to bind to the cells surface at 4° C. for 30 minutes. Next, the cells were activated at 37° C. for 10 minutes, and then lysed with RIPA buffer, followed by Western blotting using anti-phosphorylated ZAP70/phosphorylated Erk antibodies.

As shown in FIG. 14, it could be confirmed that the amounts of phosphorylated ZAP70 and Erk in the cells treated with the ntBAF57-ΔPH recombinant fusion protein or cyclosporin A decreased compared to those in the T cells activated using the anti-CD3/CD28 antibody.

In order to confirm whether the tBAF57-PH protein would also be effective in human T cells in addition to mouse T cells, $2\times10^6$ Jurkat T cells were treated with the ntBAF57-ΔPH recombinant fusion protein (1 μM or 4 μM) for 1 hour at 37° C., and then incubated with anti-CD3/CD28 antibody at 4° C. for 30 minutes, followed by activation at 37° C. for 10 minutes. Next, the cells were lysed with RIPA buffer, and then subjected to Western blotting using anti-Erk/Akt antibodies and phosphorylated Erk and Akt antibodies.

As shown in FIG. 15, it could be confirmed that the expression levels of non-phosphorylated Erk and Akt were not changed by the ntBAF57-ΔPH recombinant fusion protein, but the expression levels of phosphorylated Erk and Akt in the group treated with the ntBAF57-ΔPH recombinant fusion protein or cyclosporin A significantly decreased compared to those in the activated T cells.

[Example 6] Evaluation of Inhibitory Effect on Expression of Transcription Factors Involved in T-Cell Activation and Proliferation In Example 5 above, it was confirmed that the recombinant fusion protein exhibited an inhibitory effect on the phosphorylation of CD3/CD28 receptor downstream signaling proteins in T cells. Equally, an experiment was performed to confirm how does the ntBAF57-ΔPH recombinant fusion protein affect the expression or phosphorylation for function of major transcription factors (NFAT, NF-kB, and AP-1) that transcribe proteins involved in T cell activation and proliferation. Specifically, mouse naïve CD4+ T cells were activated by anti-CD3 and CD28 antibody (5 μg/ml), and then treated with each of the ntBAF57-ΔPH recombinant fusion protein (1 μM or 4 μM) and cyclosporin A and cultured for 24 hours at 37° C. Next, to measure the expression and phosphorylation of transcription factors in the cells, the cells were fixed, and then anti-NFAT1, p65, c-Fos and phospho c-Fos antibodies were added thereto, and transcription factors in the cells were stained with APC fluorescence-labeled secondary antibodies. The expression levels of NFAT1, p65, c-Fos and phospho c-Fos in the cells were measured by flow cytometry, and the results are shown in FIGS. 16 to 19.

As shown in FIGS. 16 to 19, it was confirmed that the expression levels of NFAT1, p65, c-Fos and phospho c-Fos in the cells treated with the ntBAF57-ΔPH recombinant fusion protein decreased compared to those in the activated T cells to the expressed levels of these transcription factors in naïve T cells, and were similar to those in the cells treated with cyclosporin A.

From the above results, it could be seen that the ntBAF57-ΔPH recombinant fusion protein played an important role in the T cell receptor downstream signaling system and also inhibited the basic T-cell activation mechanism by regulating the expression of transcription factors.

[Example 7] Relationship Between tBAF57-PH Protein and BAF Complex in Cells

In order to examine whether BAF57 protein is degraded by proteasomes if the stability of the protein is not ensured because BAF57 binds to another BAF complex subunit BAF155 in cells, an experiment was performed to examine whether the ntBAF57-ΔPH recombinant fusion protein would competitively inhibit a BAF complex by interaction with the other BAF complex subunit.

1. Examination of Inhibition of BAF155 Expression

Specifically, mouse naïve CD4+ T cells were activated by anti-CD3/CD28 antibody, and at the same time, treated with the ntBAF57-ΔPH recombinant fusion protein, followed by culture for 24 hours. Next, the cells were lysed with RIPA buffer, and anti-BAF155 antibody was allowed to bind to BAF155 in the cells for 12 hours at 4° C., and then the BAF155-bound antibody was immunoprecipitated with protein A beads. In order to examine whether the delivered ntBAF57-ΔPH recombinant fusion protein would be present in the precipitated BAF155 complex, Western blotting was performed using anti-FLAG antibody, and the results are shown in FIG. 20.

As shown in FIG. 20, it was confirmed that FLAG was detected only in the cells treated with the ntBAF57-ΔPH recombinant fusion protein. In addition, it could be confirmed that the expression level of BAF155 was higher in the activated T cells than in the naïve T cells, but when the cells were treated with the ntBAF57-ΔPH recombinant fusion protein, the expression level of BAF155 in the cells did not increase.

2. Examination of Inhibition of BAF57 Expression

In addition, in order to examine whether the ntBAF57-ΔPH recombinant fusion protein would decrease the level of BAF57 in cells by competition with BAF57 for binding to BAF155 in the cells, the following experiment was performed. Specifically, naïve CD4+ T cells were activated and, at the same time, treated with the ntBAF57-ΔPH recombinant fusion protein, followed by culture for 24 hours. Next, to analyze the expression level of BAF57 in the cells, the cells were fixed, and then treated with anti-BAF57 antibody, and the expression level of BAF57 in the cells was analyzed.

As a result, as shown in FIGS. 21 and 22, it could be confirmed that the expression level of BAF57 in the cells increased within 1 week after application of the activation signal. However, it could be confirmed that the expression level of BAF57 in the cells treated with the ntBAF57-ΔPH recombinant fusion protein decreased.

[Example 8] Examination of the Change in Expression Levels of BAF57 mRNA and BAF155 mRNA by ntBAF57-PH Recombinant Fusion Protein In order to examine whether the effect of the ntBAF57-PH recombinant fusion protein that decreases the expression level of BAF57 or BAF155 protein in the cells would be attributable to a decrease in the expression level at the gene level, total RNA was extracted using TRIzol from naïve CD4+ T cells, T cells activated for 1 day, and cells treated with 2 μM of the ntBAF57-PH recombinant fusion protein during activation. Next, from the total RNA, single strand cDNA was synthesized using MMLV reverse transcriptase, and then RT-PCR was performed using Ex Taq polymerase (40 cycles, each consisting of 30 sec at 95° C., 30 sec at 60° C., and 30 sec at 72° C.). The sequences of primers used are shown in Table 1 below. Next, bands were confirmed by electrophoresis on gel.

As shown in FIG. 23, it was confirmed that the mRNA expression levels of BAF57 and BAF155 in the T cells activated by CD3/28 increased, but there was no change in the mRNA expression levels of BAF57 and BAF155 in the cells treated with the ntBAF57-PH recombinant fusion protein, unlike the case of Example 7.

TABLE 1

| Kind of primer | Sequence |
|---|---|
| BAF57 forward primer | 5'-TATGCCCCACCTCCCAC-3' |
| BAF57 reverse primer | 5'-GGTCAGGGTTGGAAGCC-3' |
| BAF155 forward primer | 5'-GGTGCTAGTGCTGGAAGG-3' |
| BAF155 reverse primer | 5'-CAGTGCTCATCACCGGG-3' |
| GAPDH forward primer | 5'-AACTTTGGCATTGTGGAAGG-3' |
| GAPDH reverse primer | 5'-ACACATTGGGGGTAGGAAC-3' |

[Example 9] Analysis of the Mechanism by Which ntBAF57-PH Recombinant Fusion Protein Degrades BAF57 and BAF155 Proteins in Cells Previous studies showed that BAF155 protein ensures its stability against a protein degradation mechanism by binding to BAF57 in the cells and is degraded by proteasomes if it does not bind to BAF57. Based on this fact, the mechanism by which BAF57 and BAF155 proteins are degraded by treatment with the ntBAF57-PH recombinant fusion protein was analyzed. Specifically, naïve CD4+ T cells were activated, and then treated with the proteasome inhibitor MG132 or other lysosomal inhibitor $NH_4C1$ (another protein degradation mechanism) together with the ntBAF57-PH recombinant fusion protein.

As a result, as shown in FIG. 24, it could be confirmed that the expression level of BAF57 in the cells treated with the ntBAF57-PH recombinant fusion protein decreased, but the expression levels of BAF57 and the activation marker CD69 in the cells treated with MG132 increased in a concentration dependent manner. However, there was no change in the expression levels of BAF57 and CD69 in the cells treated with $NH_4C1$.

In addition, as shown in FIG. 25, it could be confirmed that the expression level of BAF155 in the cells treated with the ntBAF57-PH recombinant fusion protein decreased, whereas the expression level of BAF155 in the cells treated with MG132 increased in a concentration-dependent manner.

Therefore, it could be seen that the mechanism by which BAF57 and BAF155 proteins are degraded by the ntBAF57-PH recombinant fusion protein was attributable to proteasomes.

[Example 10] Evaluation of Therapeutic Effect of ntBAF57-PH Recombinant Fusion Protein on LPS-Induced Sepsis Mouse Model In order to examine whether the effect of the ntBAF57-PH recombinant fusion protein that strongly inhibits T-cell activation in vitro would also be exhibited in vivo, an LPS infection-induced sepsis mouse model was used. As shown in FIG. 26, 7-week-old C57BL/6 female mice were injected intraperitoneally with LPS at a dose of 15 mg/kg, and at 2 and 12 hours after the injection, 25 μg or 100 μg of each of the ntBAF57-PH recombinant fusion protein and BAF57-PH recombinant fusion protein constructed in Example 1 was injected intraperitoneally into the mice. Next, the survival rate of the mice was measured up to 144 hours, and the results are shown in FIG. 27. At 48 hours, the concentrations of the inflammatory cytokines TNF-α and IL-1β in the mouse serum were measured, and the results are shown in FIGS. 28 and 29. In addition, the proportion of T cells in the mouse splenocytes and the expression level of BAF57 protein were analyzed by flow cytometry, and the results are shown in FIGS. 30 and 31, respectively.

As shown in FIG. 27, it could be confirmed that when the sepsis mouse model was treated with the ntBAF57-PH recombinant fusion protein, the survival rate of the mice increased.

In addition, as shown in FIGS. 28 and 29, it could be confirmed that when the sepsis mouse model was treated with the ntBAF57-PH recombinant fusion protein, the concentrations of TNF-α and IL-1β in the mouse serum significantly decreased.

In addition, as shown in FIGS. 30 and 31, it could be confirmed that when the sepsis mouse model was treated with the ntBAF57-PH recombinant fusion protein, the proportion of the CD4+CD69 T cells in the mouse splenocytes decreased in a manner dependent on the concentration of the recombinant fusion protein, and the expression level of BAF57 protein in the CD4+ T cells also decreased.

As described above, the fusion protein provided in the present disclosure is capable of effectively preventing, ameliorating or treating various diseases such as inflammatory disease, immune-related disease or cancer.

Although the present disclosure has been described in detail with reference to the specific features, it will be apparent to those skilled in the art that this description is only of a preferred embodiment thereof, and does not limit the scope of the present disclosure. Thus, the substantial scope of the present disclosure will be defined by the appended claims and equivalents thereof.

What is claimed is:

1. A fusion protein comprising: a BAF57 (BRG1 or HBRM-associated factors 57) protein fragment consisting of the amino acid sequence represented by SEQ ID NO: 3 and a protein transduction domain.

2. The fusion protein of claim 1, wherein part of the BAF57 protein is encoded by the nucleotide sequence represented by SEQ ID NO: 4.

3. The fusion protein of claim 1, wherein the protein transduction domain is selected from the group consisting of Hph-1, Mph-1, Sim-2, Tat, VP22, Antp (antennapedia), Pep-1 (peptide-1), PTD-5 (protein transduction domain-5), MAP, K-FGF, penetratin, transportan, polyarginine, 11R, 7R and CTP (cytoplamic transduction peptide).

4. The fusion protein of claim 1, wherein the protein transduction domain is linked to the N-terminus of the BAF57 protein fragment.

5. The fusion protein of claim 1, further comprising a tag for separation and purification.

6. The fusion protein of claim 5, wherein the tag is at least one of an affinity tag and an epitope tag.

7. The fusion protein of claim 1, wherein the fusion protein consists of the amino acid sequence represented by any one of SEQ ID NOs: 9 to 11.

8. A nucleic acid molecule encoding the fusion protein of claim 1.

9. The nucleic acid molecule of claim 8, wherein the nucleic acid molecule consists of the nucleotide sequence represented by any one of SEQ ID NOs: 12 to 14.

10. An expression vector in which the nucleic acid molecule of claim 9 is inserted.

11. A host cell transformed with the expression vector of claim 10.

12. A method for treating sepsis in a subject comprising administering a pharmaceutically effective amount of the fusion protein of claim 1 to the subject.

* * * * *

SEQUENCE LISTING

<160> NUMBER OF SEQ ID NOS: 22

<210> SEQ ID NO 1

```
<211> LENGTH: 411
<212> TYPE: PRT
<213> ORGANISM: Homo sapiens

<400> SEQUENCE: 1

Met Ser Lys Arg Pro Ser Tyr Ala Pro Pro Pro Thr Pro Ala Pro Ala
1               5                   10                  15

Thr Gln Met Pro Ser Thr Pro Gly Phe Val Gly Tyr Asn Pro Tyr Ser
            20                  25                  30

His Leu Ala Tyr Asn Asn Tyr Arg Leu Gly Gly Asn Pro Gly Thr Asn
        35                  40                  45

Ser Arg Val Thr Ala Ser Ser Gly Ile Thr Ile Pro Lys Pro Pro Lys
    50                  55                  60

Pro Pro Asp Lys Pro Leu Met Pro Tyr Met Arg Tyr Ser Arg Lys Val
65                  70                  75                  80

Trp Asp Gln Val Lys Ala Ser Asn Pro Asp Leu Lys Leu Trp Glu Ile
                85                  90                  95

Gly Lys Ile Ile Gly Gly Met Trp Arg Asp Leu Thr Asp Glu Glu Lys
            100                 105                 110

Gln Glu Tyr Leu Asn Glu Tyr Glu Ala Glu Lys Ile Glu Tyr Asn Glu
        115                 120                 125

Ser Met Lys Ala Tyr His Asn Ser Pro Ala Tyr Leu Ala Tyr Ile Asn
    130                 135                 140

Ala Lys Ser Arg Ala Glu Ala Ala Leu Glu Glu Glu Ser Arg Gln Arg
145                 150                 155                 160

Gln Ser Arg Met Glu Lys Gly Glu Pro Tyr Met Ser Ile Gln Pro Ala
                165                 170                 175

Glu Asp Pro Asp Asp Tyr Asp Asp Gly Phe Ser Met Lys His Thr Ala
            180                 185                 190

Thr Ala Arg Phe Gln Arg Asn His Arg Leu Ile Ser Glu Ile Leu Ser
        195                 200                 205

Glu Ser Val Val Pro Asp Val Arg Ser Val Val Thr Thr Ala Arg Met
    210                 215                 220

Gln Val Leu Lys Arg Gln Val Gln Ser Leu Met Val His Gln Arg Lys
225                 230                 235                 240

Leu Glu Ala Glu Leu Leu Gln Ile Glu Glu Arg His Gln Glu Lys Lys
                245                 250                 255

Arg Lys Phe Leu Glu Ser Thr Asp Ser Phe Asn Asn Glu Leu Lys Arg
            260                 265                 270

Leu Cys Gly Leu Lys Val Glu Val Asp Met Glu Lys Ile Ala Ala Glu
        275                 280                 285

Ile Ala Gln Ala Glu Glu Gln Ala Arg Lys Arg Gln Glu Glu Arg Glu
    290                 295                 300

Lys Glu Ala Ala Glu Gln Ala Glu Arg Ser Gln Ser Ser Ile Val Pro
305                 310                 315                 320

Glu Glu Glu Gln Ala Ala Asn Lys Gly Glu Glu Lys Lys Asp Asp Glu
                325                 330                 335

Asn Ile Pro Met Glu Thr Glu Glu Thr His Leu Glu Glu Thr Thr Glu
            340                 345                 350

Ser Gln Gln Asn Gly Glu Glu Gly Thr Ser Thr Pro Glu Asp Lys Glu
        355                 360                 365

Ser Gly Gln Glu Gly Val Asp Ser Met Ala Glu Glu Gly Thr Ser Asp
    370                 375                 380

Ser Asn Thr Gly Ser Glu Ser Asn Ser Ala Thr Val Glu Glu Pro Pro
```

385 390 395 400

Thr Asp Pro Ile Pro Glu Asp Glu Lys Lys Glu
405 410

<210> SEQ ID NO 2
<211> LENGTH: 1233
<212> TYPE: DNA
<213> ORGANISM: Homo sapiens

<400> SEQUENCE: 2
atgtcaaaaa gaccatctta tgccccacct cccaccccag ctcctgcaac acaaatgccc 60
agcacaccag ggtttgtggg atacaatcca tacagtcatc tcgcctacaa caactacagg 120
ctgggaggga acccgggcac caacagccgg gtcacggcat cctctggtat cacgattcca 180
aaacccccaa agccaccaga taagccgctg atgccctaca tgaggtacag cagaaaggtc 240
tgggaccaag taaaggcttc caaccctgac ctaaagttgt gggagattgg caagattatt 300
ggtggcatgt ggcgagatct cactgatgaa gaaaaacaag aatatttaaa cgaatacgaa 360
gcagaaaaga tagagtacaa tgaatctatg aaggcctatc ataattcccc cgcgtacctt 420
gcttacataa atgcaaaaag tcgtgcagaa gctgctttag aggaagaaag tcgacagaga 480
caatctcgca tggagaaagg agaaccgtac atgagcattc agcctgctga agatccagat 540
gattatgatg atggcttttc aatgaagcat acagccaccg cccgtttcca gagaaaccac 600
cgcctcatca gtgaaattct tagtgagagt gtggtgccag acgttcggtc agttgtcaca 660
acagctagaa tgcaggtcct caaacggcag gtccagtcct taatggttca tcagcgaaaa 720
ctagaagctg aacttcttca aatagaggaa cgacaccagg agaagaagag gaaattcctg 780
gaaagcacag attcatttaa caatgaactt aaaaggttgt gcggtctgaa agtagaagtg 840
gatatggaga aaattgcagc tgagattgca caggcagagg aacaggcccg caaaaggcag 900
gaggaaaggg agaaggaggc cgcagagcaa gctgagcgca gtcagagcag catcgttcct 960
gaggaagaac aagcagctaa caaaggcgag gagaagaaag acgacgagaa cattccgatg 1020
gagacagagg agacacacct tgaagaaaca acagagagcc aacagaatgg tgaagaaggc 1080
acgtctactc ctgaggacaa ggagagtggg caggaggggg tcgacagtat ggcagaggaa 1140
ggaaccagtg atagtaacac tggctcggag agcaacagtg caacagtgga ggagccacca 1200
acagatccca taccagaaga tgagaaaaaa gaa 1233

<210> SEQ ID NO 3
<211> LENGTH: 280
<212> TYPE: PRT
<213> ORGANISM: Homo sapiens

<400> SEQUENCE: 3

Ala Tyr His Asn Ser Pro Ala Tyr Leu Ala Tyr Ile Asn Ala Lys Ser
1 5 10 15

Arg Ala Glu Ala Ala Leu Glu Glu Glu Ser Arg Gln Arg Gln Ser Arg
20 25 30

Met Glu Lys Gly Glu Pro Tyr Met Ser Ile Gln Pro Ala Glu Asp Pro
35 40 45

Asp Asp Tyr Asp Asp Gly Phe Ser Met Lys His Thr Ala Thr Ala Arg
50 55 60

Phe Gln Arg Asn His Arg Leu Ile Ser Glu Ile Leu Ser Glu Ser Val
65 70 75 80

Val Pro Asp Val Arg Ser Val Val Thr Thr Ala Arg Met Gln Val Leu

```
                85                  90                  95

Lys Arg Gln Val Gln Ser Leu Met Val His Gln Arg Lys Leu Glu Ala
            100                 105                 110

Glu Leu Leu Gln Ile Glu Glu Arg His Gln Glu Lys Lys Arg Lys Phe
        115                 120                 125

Leu Glu Ser Thr Asp Ser Phe Asn Asn Glu Leu Lys Arg Leu Cys Gly
    130                 135                 140

Leu Lys Val Glu Val Asp Met Glu Lys Ile Ala Ala Glu Ile Ala Gln
145                 150                 155                 160

Ala Glu Glu Gln Ala Arg Lys Arg Gln Glu Glu Arg Glu Lys Glu Ala
                165                 170                 175

Ala Glu Gln Ala Glu Arg Ser Gln Ser Ser Ile Val Pro Glu Glu Glu
            180                 185                 190

Gln Ala Ala Asn Lys Gly Glu Glu Lys Lys Asp Asp Glu Asn Ile Pro
        195                 200                 205

Met Glu Thr Glu Glu Thr His Leu Glu Glu Thr Thr Glu Ser Gln Gln
    210                 215                 220

Asn Gly Glu Glu Gly Thr Ser Thr Pro Glu Asp Lys Glu Ser Gly Gln
225                 230                 235                 240

Glu Gly Val Asp Ser Met Ala Glu Glu Gly Thr Ser Asp Ser Asn Thr
                245                 250                 255

Gly Ser Glu Ser Asn Ser Ala Thr Val Glu Glu Pro Pro Thr Asp Pro
            260                 265                 270

Ile Pro Glu Asp Glu Lys Lys Glu
        275                 280
```

<210> SEQ ID NO 4
<211> LENGTH: 840
<212> TYPE: DNA
<213> ORGANISM: Homo sapiens

<400> SEQUENCE: 4

```
gcctatcata attcccccgc gtaccttgct tacataaatg caaaaagtcg tgcagaagct     60

gctttagagg aagaaagtcg acagagacaa tctcgcatgg agaaaggaga accgtacatg    120

agcattcagc ctgctgaaga tccagatgat tatgatgatg gcttttcaat gaagcataca    180

gccaccgccc gtttccagag aaaccaccgc ctcatcagtg aaattcttag tgagagtgtg    240

gtgccagacg ttcggtcagt tgtcacaaca gctagaatgc aggtcctcaa acggcaggtc    300

cagtccttaa tggttcatca gcgaaaacta gaagctgaac ttcttcaaat agaggaacga    360

caccaggaga agaagaggaa attcctggaa agcacagatt catttaacaa tgaacttaaa    420

aggttgtgcg gtctgaaagt agaagtggat atggagaaaa ttgcagctga gattgcacag    480

gcagaggaac aggcccgcaa aaggcaggag gaaagggaga aggaggccgc agagcaagct    540

gagcgcagtc agagcagcat cgttcctgag gaagaacaag cagctaacaa aggcgaggag    600

aagaaagacg acgagaacat tccgatggag acagaggaga cacaccttga agaaacaaca    660

gagagccaac agaatggtga agaaggcacg tctactcctg aggacaagga gagtgggcag    720

gagggggtcg acagtatggc agaggaagga accagtgata gtaacactgg ctcggagagc    780

aacagtgcaa cagtggagga gccaccaaca gatcccatac cagaagatga gaaaaaagaa    840
```

<210> SEQ ID NO 5
<211> LENGTH: 11
<212> TYPE: PRT
<213> ORGANISM: Artificial Sequence

```
<220> FEATURE:
<223> OTHER INFORMATION: Amino acid sequence of Hph-1

<400> SEQUENCE: 5

Tyr Ala Arg Val Arg Arg Arg Gly Pro Arg Arg
1               5                   10


<210> SEQ ID NO 6
<211> LENGTH: 33
<212> TYPE: DNA
<213> ORGANISM: Artificial Sequence
<220> FEATURE:
<223> OTHER INFORMATION: Nucleotide sequence of Hph-1

<400> SEQUENCE: 6

tatgcacgtg ttcggaggcg tggaccccgc cgc                                   33


<210> SEQ ID NO 7
<211> LENGTH: 8
<212> TYPE: PRT
<213> ORGANISM: Artificial Sequence
<220> FEATURE:
<223> OTHER INFORMATION: Amino acid sequence of FLAG tag

<400> SEQUENCE: 7

Asp Tyr Lys Asp Asp Asp Asp Lys
1               5


<210> SEQ ID NO 8
<211> LENGTH: 24
<212> TYPE: DNA
<213> ORGANISM: Artificial Sequence
<220> FEATURE:
<223> OTHER INFORMATION: Nucleotide sequence of FLAG tag

<400> SEQUENCE: 8

gactacaagg acgacgatga caag                                             24


<210> SEQ ID NO 9
<211> LENGTH: 291
<212> TYPE: PRT
<213> ORGANISM: Artificial Sequence
<220> FEATURE:
<223> OTHER INFORMATION: Amino acid sequence of fusion protein

<400> SEQUENCE: 9

Tyr Ala Arg Val Arg Arg Arg Gly Pro Arg Arg Ala Tyr His Asn Ser
1               5                   10                  15

Pro Ala Tyr Leu Ala Tyr Ile Asn Ala Lys Ser Arg Ala Glu Ala Ala
            20                  25                  30

Leu Glu Glu Glu Ser Arg Gln Arg Gln Ser Arg Met Glu Lys Gly Glu
        35                  40                  45

Pro Tyr Met Ser Ile Gln Pro Ala Glu Asp Pro Asp Asp Tyr Asp Asp
    50                  55                  60

Gly Phe Ser Met Lys His Thr Ala Thr Ala Arg Phe Gln Arg Asn His
65                  70                  75                  80

Arg Leu Ile Ser Glu Ile Leu Ser Glu Ser Val Val Pro Asp Val Arg
                85                  90                  95

Ser Val Val Thr Thr Ala Arg Met Gln Val Leu Lys Arg Gln Val Gln
            100                 105                 110

Ser Leu Met Val His Gln Arg Lys Leu Glu Ala Glu Leu Leu Gln Ile
        115                 120                 125
```

```
Glu Glu Arg His Gln Glu Lys Lys Arg Lys Phe Leu Glu Ser Thr Asp
    130                 135                 140

Ser Phe Asn Asn Glu Leu Lys Arg Leu Cys Gly Leu Lys Val Glu Val
145                 150                 155                 160

Asp Met Glu Lys Ile Ala Ala Glu Ile Ala Gln Ala Glu Glu Gln Ala
                165                 170                 175

Arg Lys Arg Gln Glu Glu Arg Glu Lys Glu Ala Ala Glu Gln Ala Glu
            180                 185                 190

Arg Ser Gln Ser Ser Ile Val Pro Glu Glu Glu Gln Ala Ala Asn Lys
        195                 200                 205

Gly Glu Glu Lys Lys Asp Asp Glu Asn Ile Pro Met Glu Thr Glu Glu
    210                 215                 220

Thr His Leu Glu Glu Thr Thr Glu Ser Gln Gln Asn Gly Glu Glu Gly
225                 230                 235                 240

Thr Ser Thr Pro Glu Asp Lys Glu Ser Gly Gln Glu Gly Val Asp Ser
                245                 250                 255

Met Ala Glu Glu Gly Thr Ser Asp Ser Asn Thr Gly Ser Glu Ser Asn
            260                 265                 270

Ser Ala Thr Val Glu Glu Pro Pro Thr Asp Pro Ile Pro Glu Asp Glu
        275                 280                 285

Lys Lys Glu
    290


<210> SEQ ID NO 10
<211> LENGTH: 299
<212> TYPE: PRT
<213> ORGANISM: Artificial Sequence
<220> FEATURE:
<223> OTHER INFORMATION: Amino acid sequence of fusion protein

<400> SEQUENCE: 10

Tyr Ala Arg Val Arg Arg Arg Gly Pro Arg Arg Asp Tyr Lys Asp Asp
1               5                   10                  15

Asp Asp Lys Ala Tyr His Asn Ser Pro Ala Tyr Leu Ala Tyr Ile Asn
            20                  25                  30

Ala Lys Ser Arg Ala Glu Ala Ala Leu Glu Glu Glu Ser Arg Gln Arg
        35                  40                  45

Gln Ser Arg Met Glu Lys Gly Glu Pro Tyr Met Ser Ile Gln Pro Ala
    50                  55                  60

Glu Asp Pro Asp Asp Tyr Asp Asp Gly Phe Ser Met Lys His Thr Ala
65                  70                  75                  80

Thr Ala Arg Phe Gln Arg Asn His Arg Leu Ile Ser Glu Ile Leu Ser
                85                  90                  95

Glu Ser Val Val Pro Asp Val Arg Ser Val Val Thr Thr Ala Arg Met
            100                 105                 110

Gln Val Leu Lys Arg Gln Val Gln Ser Leu Met Val His Gln Arg Lys
        115                 120                 125

Leu Glu Ala Glu Leu Leu Gln Ile Glu Glu Arg His Gln Glu Lys Lys
    130                 135                 140

Arg Lys Phe Leu Glu Ser Thr Asp Ser Phe Asn Asn Glu Leu Lys Arg
145                 150                 155                 160

Leu Cys Gly Leu Lys Val Glu Val Asp Met Glu Lys Ile Ala Ala Glu
                165                 170                 175

Ile Ala Gln Ala Glu Glu Gln Ala Arg Lys Arg Gln Glu Glu Arg Glu
            180                 185                 190
```

```
Lys Glu Ala Ala Glu Gln Ala Glu Arg Ser Gln Ser Ser Ile Val Pro
        195                 200                 205

Glu Glu Glu Gln Ala Ala Asn Lys Gly Glu Glu Lys Lys Asp Asp Glu
    210                 215                 220

Asn Ile Pro Met Glu Thr Glu Glu Thr His Leu Glu Glu Thr Thr Glu
225                 230                 235                 240

Ser Gln Gln Asn Gly Glu Glu Gly Thr Ser Thr Pro Glu Asp Lys Glu
                245                 250                 255

Ser Gly Gln Glu Gly Val Asp Ser Met Ala Glu Glu Gly Thr Ser Asp
            260                 265                 270

Ser Asn Thr Gly Ser Glu Ser Asn Ser Ala Thr Val Glu Glu Pro Pro
        275                 280                 285

Thr Asp Pro Ile Pro Glu Asp Glu Lys Lys Glu
    290                 295


<210> SEQ ID NO 11
<211> LENGTH: 327
<212> TYPE: PRT
<213> ORGANISM: Artificial Sequence
<220> FEATURE:
<223> OTHER INFORMATION: Amino acid sequence of ntBAF57-PH fusion
      protein

<400> SEQUENCE: 11

Met Gly Ser Ser His His His His His His Ser Ser Gly Leu Val Pro
1               5                   10                  15

Arg Gly Ser His Met Ala Ser Gly Tyr Ala Arg Val Arg Arg Arg Gly
            20                  25                  30

Pro Arg Arg Gly Asp Tyr Lys Asp Asp Asp Asp Lys Glu Phe Gly Ala
        35                  40                  45

Tyr His Asn Ser Pro Ala Tyr Leu Ala Tyr Ile Asn Ala Lys Ser Arg
    50                  55                  60

Ala Glu Ala Ala Leu Glu Glu Glu Ser Arg Gln Arg Gln Ser Arg Met
65                  70                  75                  80

Glu Lys Gly Glu Pro Tyr Met Ser Ile Gln Pro Ala Glu Asp Pro Asp
                85                  90                  95

Asp Tyr Asp Asp Gly Phe Ser Met Lys His Thr Ala Thr Ala Arg Phe
            100                 105                 110

Gln Arg Asn His Arg Leu Ile Ser Glu Ile Leu Ser Glu Ser Val Val
        115                 120                 125

Pro Asp Val Arg Ser Val Val Thr Thr Ala Arg Met Gln Val Leu Lys
    130                 135                 140

Arg Gln Val Gln Ser Leu Met Val His Gln Arg Lys Leu Glu Ala Glu
145                 150                 155                 160

Leu Leu Gln Ile Glu Glu Arg His Gln Glu Lys Lys Arg Lys Phe Leu
                165                 170                 175

Glu Ser Thr Asp Ser Phe Asn Asn Glu Leu Lys Arg Leu Cys Gly Leu
            180                 185                 190

Lys Val Glu Val Asp Met Glu Lys Ile Ala Ala Glu Ile Ala Gln Ala
        195                 200                 205

Glu Glu Gln Ala Arg Lys Arg Gln Glu Glu Arg Glu Lys Glu Ala Ala
    210                 215                 220

Glu Gln Ala Glu Arg Ser Gln Ser Ser Ile Val Pro Glu Glu Glu Gln
225                 230                 235                 240

Ala Ala Asn Lys Gly Glu Glu Lys Lys Asp Asp Glu Asn Ile Pro Met
                245                 250                 255
```

```
Glu Thr Glu Glu Thr His Leu Glu Glu Thr Thr Glu Ser Gln Gln Asn
            260                 265                 270

Gly Glu Glu Gly Thr Ser Thr Pro Glu Asp Lys Glu Ser Gly Gln Glu
        275                 280                 285

Gly Val Asp Ser Met Ala Glu Glu Gly Thr Ser Asp Ser Asn Thr Gly
    290                 295                 300

Ser Glu Ser Asn Ser Ala Thr Val Glu Glu Pro Pro Thr Asp Pro Ile
305                 310                 315                 320

Pro Glu Asp Glu Lys Lys Glu
                325
```

<210> SEQ ID NO 12
<211> LENGTH: 873
<212> TYPE: DNA
<213> ORGANISM: Artificial Sequence
<220> FEATURE:
<223> OTHER INFORMATION: Nucleotide sequence of fusion protein

<400> SEQUENCE: 12

```
tatgcacgtg ttcggaggcg tggaccccgc cgcgcctatc ataattcccc cgcgtacctt     60

gcttacataa atgcaaaaag tcgtgcagaa gctgctttag aggaagaaag tcgacagaga    120

caatctcgca tggagaaagg agaaccgtac atgagcattc agcctgctga agatccagat    180

gattatgatg atggcttttc aatgaagcat acagccaccg cccgtttcca gagaaaccac    240

cgcctcatca gtgaaattct tagtgagagt gtggtgccag acgttcggtc agttgtcaca    300

acagctagaa tgcaggtcct caaacggcag gtccagtcct taatggttca tcagcgaaaa    360

ctagaagctg aacttcttca aatagaggaa cgacaccagg agaagaagag gaaattcctg    420

gaaagcacag attcatttaa caatgaactt aaaaggttgt gcggtctgaa agtagaagtg    480

gatatggaga aaattgcagc tgagattgca caggcagagg aacaggcccg caaaaggcag    540

gaggaaaggg agaaggaggc cgcagagcaa gctgagcgca gtcagagcag catcgttcct    600

gaggaagaac aagcagctaa caaaggcgag gagaagaaag acgacgagaa cattccgatg    660

gagacagagg agacacacct tgaagaaaca acagagagcc aacagaatgg tgaagaaggc    720

acgtctactc ctgaggacaa ggagagtggg caggaggggg tcgacagtat ggcagaggaa    780

ggaaccagtg atagtaacac tggctcggag agcaacagtg caacagtgga ggagccacca    840

acagatccca taccagaaga tgagaaaaaa gaa                                873
```

<210> SEQ ID NO 13
<211> LENGTH: 897
<212> TYPE: DNA
<213> ORGANISM: Artificial Sequence
<220> FEATURE:
<223> OTHER INFORMATION: Nucleotide sequence of fusion protein

<400> SEQUENCE: 13

```
tatgcacgtg ttcggaggcg tggaccccgc cgcgactaca aggacgacga tgacaaggcc     60

tatcataatt cccccgcgta ccttgcttac ataaatgcaa aaagtcgtgc agaagctgct    120

ttagaggaag aaagtcgaca gagacaatct cgcatggaga aaggagaacc gtacatgagc    180

attcagcctg ctgaagatcc agatgattat gatgatggct tttcaatgaa gcatacagcc    240

accgcccgtt tccagagaaa ccaccgcctc atcagtgaaa ttcttagtga gagtgtggtg    300

ccagacgttc ggtcagttgt cacaacagct agaatgcagg tcctcaaacg gcaggtccag    360

tccttaatgg ttcatcagcg aaaactagaa gctgaacttc ttcaaataga ggaacgacac    420
```

```
caggagaaga agaggaaatt cctggaaagc acagattcat ttaacaatga acttaaaagg    480

ttgtgcggtc tgaaagtaga agtggatatg gagaaaattg cagctgagat tgcacaggca    540

gaggaacagg cccgcaaaag gcaggaggaa agggagaagg aggccgcaga gcaagctgag    600

cgcagtcaga gcagcatcgt tcctgaggaa gaacaagcag ctaacaaagg cgaggagaag    660

aaagacgacg agaacattcc gatggagaca gaggagacac accttgaaga aacaacagag    720

agccaacaga atggtgaaga aggcacgtct actcctgagg acaaggagag tgggcaggag    780

ggggtcgaca gtatggcaga ggaaggaacc agtgatagta acactggctc ggagagcaac    840

agtgcaacag tggaggagcc accaacagat cccataccag aagatgagaa aaaagaa       897
```

<210> SEQ ID NO 14
<211> LENGTH: 984
<212> TYPE: DNA
<213> ORGANISM: Artificial Sequence
<220> FEATURE:
<223> OTHER INFORMATION: Nucleotide sequence of ntBAF57-PH fusion protein

<400> SEQUENCE: 14

```
atgggcagca gccatcatca tcatcatcac agcagcggcc tggtgccgcg cggcagccat     60

atggctagcg gctatgcacg tgttcggagg cgtggacccc gccgcggcga ctacaaggac    120

gacgatgaca aggaattcgg agcctatcat aattcccccg cgtaccttgc ttacataaat    180

gcaaaaagtc gtgcagaagc tgctttagag gaagaaagtc gacagagaca atctcgcatg    240

gagaaaggag aaccgtacat gagcattcag cctgctgaag atccagatga ttatgatgat    300

ggcttttcaa tgaagcatac agccaccgcc cgtttccaga gaaaccaccg cctcatcagt    360

gaaattctta gtgagagtgt ggtgccagac gttcggtcag ttgtcacaac agctagaatg    420

caggtcctca aacggcaggt ccagtcctta atggttcatc agcgaaaact agaagctgaa    480

cttcttcaaa tagaggaacg acaccaggag aagaagagga aattcctgga aagcacagat    540

tcatttaaca atgaacttaa aaggttgtgc ggtctgaaag tagaagtgga tatggagaaa    600

attgcagctg agattgcaca ggcagaggaa caggcccgca aaaggcagga ggaaagggag    660

aaggaggccg cagagcaagc tgagcgcagt cagagcagca tcgttcctga ggaagaacaa    720

gcagctaaca aaggcgagga gaagaaagac gacgagaaca ttccgatgga gacagaggag    780

acacaccttg aagaaacaac agagagccaa cagaatggtg aagaaggcac gtctactcct    840

gaggacaagg agagtgggca ggagggggtc gacagtatgg cagaggaagg aaccagtgat    900

agtaacactg gctcggagag caacagtgca acagtggagg agccaccaac agatcccata    960

ccagaagatg agaaaaaaga atag                                           984
```

<210> SEQ ID NO 15
<211> LENGTH: 314
<212> TYPE: PRT
<213> ORGANISM: Artificial Sequence
<220> FEATURE:
<223> OTHER INFORMATION: Amino acid sequence of BAF57-PH fusion protein

<400> SEQUENCE: 15

```
Met Gly Ser Ser His His His His His His Ser Ser Gly Leu Val Pro
1               5                   10                  15

Arg Gly Ser His Met Ala Ser Asp Tyr Lys Asp Asp Asp Asp Lys Glu
            20                  25                  30

Phe Gly Ala Tyr His Asn Ser Pro Ala Tyr Leu Ala Tyr Ile Asn Ala
```

```
        35                  40                  45

Lys Ser Arg Ala Glu Ala Ala Leu Glu Glu Glu Ser Arg Gln Arg Gln
    50                  55                  60

Ser Arg Met Glu Lys Gly Glu Pro Tyr Met Ser Ile Gln Pro Ala Glu
65                  70                  75                  80

Asp Pro Asp Asp Tyr Asp Asp Gly Phe Ser Met Lys His Thr Ala Thr
                85                  90                  95

Ala Arg Phe Gln Arg Asn His Arg Leu Ile Ser Glu Ile Leu Ser Glu
            100                 105                 110

Ser Val Val Pro Asp Val Arg Ser Val Val Thr Thr Ala Arg Met Gln
        115                 120                 125

Val Leu Lys Arg Gln Val Gln Ser Leu Met Val His Gln Arg Lys Leu
    130                 135                 140

Glu Ala Glu Leu Leu Gln Ile Glu Glu Arg His Gln Glu Lys Lys Arg
145                 150                 155                 160

Glu Phe Leu Glu Ser Thr Asp Ser Phe Asn Asn Glu Leu Lys Arg Leu
                165                 170                 175

Cys Gly Leu Lys Val Glu Val Asp Met Glu Lys Ile Ala Ala Glu Ile
            180                 185                 190

Ala Gln Ala Glu Glu Gln Ala Arg Lys Arg Gln Glu Glu Arg Glu Lys
        195                 200                 205

Glu Ala Ala Glu Gln Ala Glu Arg Ser Gln Ser Ser Ile Val Pro Glu
    210                 215                 220

Glu Glu Gln Ala Ala Asn Lys Gly Glu Glu Lys Lys Asp Asp Glu Asn
225                 230                 235                 240

Ile Pro Met Glu Thr Glu Glu Thr His Leu Glu Glu Thr Thr Glu Ser
                245                 250                 255

Gln Gln Asn Gly Glu Glu Gly Thr Ser Thr Pro Glu Asp Lys Glu Ser
            260                 265                 270

Gly Gln Glu Gly Val Asp Ser Met Ala Glu Glu Gly Thr Ser Asp Ser
        275                 280                 285

Asn Thr Gly Ser Glu Ser Asn Ser Ala Thr Val Glu Glu Pro Pro Thr
    290                 295                 300

Asp Pro Ile Pro Glu Asp Glu Lys Lys Glu
305                 310
```

<210> SEQ ID NO 16
<211> LENGTH: 945
<212> TYPE: DNA
<213> ORGANISM: Artificial Sequence
<220> FEATURE:
<223> OTHER INFORMATION: Nucleotide sequence of BAF57-PH fusion protein

<400> SEQUENCE: 16

```
atgggcagca gccatcatca tcatcatcac agcagcggcc tggtgccgcg cggcagccat     60

atggctagcg actacaagga cgacgatgac aaggaattcg gagcctatca taattccccc    120

gcgtaccttg cttacataaa tgcaaaaagt cgtgcagaag ctgctttaga ggaagaaagt    180

cgacagagac aatctcgcat ggagaaagga gaaccgtaca tgagcattca gcctgctgaa    240

gatccagatg attatgatga tggcttttca atgaagcata cagccaccgc ccgtttccag    300

agaaaccacc gcctcatcag tgaaattctt agtgagagtg tggtgccaga cgttcggtca    360

gttgtcacaa cagctagaat gcaggtcctc aaacggcagg tccagtcctt aatggttcat    420

cagcgaaaac tagaagctga acttcttcaa atagaggaac gacaccagga gaagaagagg    480
```

```
gaattcctgg aaagcacgga ttcatttaac aatgaactta aaaggttgtg cggtctgaaa    540

gtagaagtgg atatggagaa aattgcagct gagattgcac aggcagagga acaggcccgc    600

aaaaggcagg aggaaaggga gaaggaggcc gcagagcaag ctgagcgcag tcagagcagc    660

atcgttcctg aggaagaaca agcagctaac aaaggcgagg agaagaaaga cgacgagaac    720

attccgatgg agacagagga gacacacctt gaagaaacaa cagagagcca acagaatggt    780

gaagaaggca cgtctactcc tgaggacaag gagagtgggc aggagggggt cgacagtatg    840

gcagaggaag gaaccagtga tagtaacact ggctcggaga gcaacagtgc aacagtggag    900

gagccaccaa cagatcccat accagaagat gagaaaaaag aatag                    945


<210> SEQ ID NO 17
<211> LENGTH: 17
<212> TYPE: DNA
<213> ORGANISM: Artificial Sequence
<220> FEATURE:
<223> OTHER INFORMATION: BAF57 forward primer

<400> SEQUENCE: 17

tatgccccac ctcccac                                                    17


<210> SEQ ID NO 18
<211> LENGTH: 17
<212> TYPE: DNA
<213> ORGANISM: Artificial Sequence
<220> FEATURE:
<223> OTHER INFORMATION: BAF57 reverse primer

<400> SEQUENCE: 18

ggtcagggtt ggaagcc                                                    17


<210> SEQ ID NO 19
<211> LENGTH: 18
<212> TYPE: DNA
<213> ORGANISM: Artificial Sequence
<220> FEATURE:
<223> OTHER INFORMATION: BAF155 forward primer

<400> SEQUENCE: 19

ggtgctagtg ctggaagg                                                   18


<210> SEQ ID NO 20
<211> LENGTH: 17
<212> TYPE: DNA
<213> ORGANISM: Artificial Sequence
<220> FEATURE:
<223> OTHER INFORMATION: BAF155 reverse primer

<400> SEQUENCE: 20

cagtgctcat caccggg                                                    17


<210> SEQ ID NO 21
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 21

aactttggca ttgtggaagg                                                 20


<210> SEQ ID NO 22
<211> LENGTH: 19
```

-continued

```
<212> TYPE: DNA
<213> ORGANISM: Artificial Sequence
<220> FEATURE:
<223> OTHER INFORMATION: GAPDH reverse primer

<400> SEQUENCE: 22

acacattggg ggtaggaac                                              19
```